(12) United States Patent
Siegel et al.

(10) Patent No.: US 9,518,049 B2
(45) Date of Patent: Dec. 13, 2016

(54) SALT FORMS OF (S)-QUINUCLIDIN-3-YL (2-(2-(4-FLUOROPHENYL)THIAZOL-4-YL)PROPAN-2-YL)CARBAMATE

(71) Applicant: Genzyme Corporation, Cambridge, MA (US)

(72) Inventors: Craig S. Siegel, Woburn, MA (US); Jin Zhao, Framingham, MA (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 14/776,432

(22) PCT Filed: Mar. 14, 2014

(86) PCT No.: PCT/US2014/027081
§ 371 (c)(1),
(2) Date: Sep. 14, 2015

(87) PCT Pub. No.: WO2014/152215
PCT Pub. Date: Sep. 25, 2014

(65) Prior Publication Data
US 2016/0039805 A1 Feb. 11, 2016

Related U.S. Application Data

(60) Provisional application No. 61/791,706, filed on Mar. 15, 2013.

(51) Int. Cl.
*C07D 453/00* (2006.01)
*C07C 59/245* (2006.01)

(52) U.S. Cl.
CPC ........... *C07D 453/00* (2013.01); *C07C 59/245* (2013.01)

(58) Field of Classification Search
CPC .................................................. C07D 453/00
USPC ........................................................ 546/133
See application file for complete search history.

(56) References Cited

U.S. PATENT DOCUMENTS

| | | | |
|---|---|---|---|
| 5,236,838 A | 8/1993 | Rasmussen et al. | |
| 5,272,071 A | 12/1993 | Chappel | |
| 5,549,892 A | 8/1996 | Friedman et al. | |
| 5,968,502 A | 10/1999 | Treco et al. | |
| 6,066,626 A | 5/2000 | Yew et al. | |
| 2011/0052559 A1 | 3/2011 | Schuchman et al. | |

FOREIGN PATENT DOCUMENTS

| | | | |
|---|---|---|---|
| WO | 2005068426 A1 | | 7/2005 |
| WO | 2006053043 A2 | | 5/2006 |
| WO | WO2010/091104 | | 8/2010 |
| WO | 2012/129084 | * | 9/2012 |
| WO | 2012129084 A2 | | 9/2012 |

OTHER PUBLICATIONS

Barton N.W., et al., "Replacement Therapy for Inherited Enzyme Deficiency—Macrophage-Targeted Glucocerebrosidase for Gaucher'S Disease," The New England Journal of Medicine, 1991, vol. 324 (21), pp. 1464-1470.
Bastin R.J., et al., "Salt Selection and Optimisation for Pharmaceutical New Chemical Entities," Organic Process Research & Development, 2000, vol. 4 (5), pp. 427-435.
Beniaminovitz A., et al., "Prevention of Rejection in Cardiac Transplantation by Blockade of the Interleukin-2 Receptor with a Monoclonal Antibody," The New England Journal of Medicine, 2000, vol. 342 (9), pp. 613-619.
Berard J.L., et al., "A Review of Interleukin-2 Receptor Antagonists in Solid Organ Transplantation," Pharmacotherapy, 1999, vol. 19 (10), pp. 1127-1137.
Branco L., et al., "Selective Deletion of Antigen-Specific, Activated T Cells by a Humanized MAB to CD2 (Medi-507) is Mediated by NK Cells," Transplantation, 1999, vol. 68 (10), pp. 1588-1596.
Caira M.R., "Crystalline Polymorphism of Organic Compounds," Topics in Current Chemistry, 1999, vol. 198, pp. 163-208.
Chirmule N., et al., "Readministration of Adenovirus Vector in Nonhuman Primate Lungs by Blockade of CD40-CD40 Ligand Interactions," Journal of Virology, 2000, vol. 74 (7), pp. 3345-3352.
Czartoryska B., et al., "Changes in Serum Chitotriosidase Activity with Cessation of Replacement Enzyme (Cerebrosidase) Administration in Gaucher Disease," Clinical Biochemistry, 2000, vol. 33 (2), pp. 147-149.
Czartoryska B., et al., "Serum Chitotriosidase Activity in Gaucher Patients on Enzyme Replacement Therapy (ERT)," Clinical Biochemistry, 1998, vol. 31 (5), pp. 417-420.
Den Tandt W.R., et al., "Marked Increase of Methylumbelliferyl-Tetra-N-Acetylchitotetraoside Hydrolase Activity in Plasma from Gaucher Disease Patients," Journal of Inherited Metabolic Disease, 1996, vol. 19 (3), pp. 344-350.
Dodelson De Kremer R., et al., "[Plasma Chitotriosidase Activity in Argentinian Patients with Gaucher Disease, Various Lysosomal Diseases and Other Inherited Metabolic Disorders]," Medicina, 1997, vol. 57 (6), pp. 677-684.
Eckhoff D.E., et al., "The Safety and Efficacy of a Two-Dose Daclizumab (Zenapax) Induction Therapy in Liver Transplant Recipients," Transplantation, 2000, vol. 69 (9), pp. 1867-1872.
Ekberg H., et al., "Daclizumab Prevents Acute Rejection and Improves Patient Survival Post Transplantation: 1 Year Pooled Analysis," Transplant International, 2000, vol. 13 (2), pp. 151-159.
El Alwani M., et al., "Regulation of the Sphingolipid Signaling Pathways in the Growing and Hypoxic Rat Heart," Prostaglandins & Other Lipid Mediators, 2005, vol. 78 (1-4), pp. 249-263.
Enquist I.B., et al., "Murine Models of Acute Neuronopathic Gaucher Disease," Proceedings of the National Academy of Sciences of the United States of America, 2007, vol. 104 (44), pp. 17483-17488.

(Continued)

*Primary Examiner* — Niloofar Rahmani
(74) *Attorney, Agent, or Firm* — Peter Korakas

(57) ABSTRACT

The present invention relates to novel salt forms of (S)-Quinuclidin-3-yl (2-(2-(4-fluorophenyl)thiazol-4-yl)propan-2-yl)carbamate useful as an inhibitor of glucosylceramide synthase (GCS) and for the treatment metabolic diseases, such as lysosomal storage diseases, either alone or in combination with enzyme replacement therapy, and for the treatment of cancer.

24 Claims, 4 Drawing Sheets

(56) References Cited

OTHER PUBLICATIONS

Fishwild D.M., et al., "Differential Effects of Administration of a Human Anti-CD4 Monoclonal Antibody, HM6G, in Nonhuman Primates," Clinical Immunology, 1999, vol. 92 (2), pp. 138-152.

Gaziev D., et al., "Chronic Graft-Versus-Host Disease: Is there an Alternative to the Conventional Treatment?," Bone Marrow Transplantation, 2000, vol. 25 (7), pp. 689-696.

Goker-Alpan O., et al., "Phenotypic Continuum in Neuronopathic Gaucher Disease: An Intermediate Phenotype Between Type 2 and Type 3," The Journal of Pediatrics, 2003, vol. 143 (2), pp. 273-276.

Grabowski G.A., et al., "Enzyme Therapy in Type 1 Gaucher Disease: Comparative Efficacy of Mannose-Terminated Glucocerebrosidase from Natural and Recombinant Sources," Annals of Internal Medicine, 1995, vol. 122 (1), pp. 33-39.

Gummert J.F., et al., "Newer Immunosuppressive Drugs: A Review," Journal of the American Society of Nephrology : Jasn, 1999, vol. 10 (6), pp. 1366-1380.

Guo Y., et al., "Elevated Plasma Chitotriosidase Activity in Various Lysosomal Storage Disorders," Journal of Inherited Metabolic Disease, 1995, vol. 18 (6), pp. 717-722.

Henry M.L., et al., "Cyclosporine and Tacrolimus (FK506): A Comparison of Efficacy and Safety Profiles," Clinical Transplantation, 1999, vol. 13 (3), pp. 209-220.

Hers H.G. "Inborn Lysosomal Diseases," Gastroenterology, 1965, vol. 48, pp. 625-633.

Hollak C.E., et al., "Marked Elevation of Plasma Chitotriosidase Activity. A Novel Hallmark of Gaucher Disease," The Journal of Clinical Investigation, 1994, vol. 93 (3), pp. 1288-1292.

Hong J.C., et al., "Immunosuppressive Agents in Organ Transplantation: Past, Present, and Future," Seminars in Nephrology, 2000, vol. 20 (2), pp 108-125.

Ideguchi M., et al., "Local Adenovirus-Mediated CTLA4-Immunoglobulin Expression Suppresses the Immune Responses to Adenovirus Vectors in the Brain," Neuroscience, 2000, vol. 95 (1), pp. 217-226.

International Preliminary Report on Patentability for Application No. PCT/US2014/027081, mailed on Sep. 15, 2015, 6 pages.

International Search Report and Written Opinion for Application No. PCT/US2014/027081, mailed on May 20, 2014, 9 pages.

Ito D., et al., "Induction of CTL Responses by Simultaneous Administration of Liposomal Peptide Vaccine with Anti-Cd40 and Anti-CTLA-4 Mab," Journal of Immunology, 2000, vol. 164 (3), pp. 1230-1235.

Kurlberg G., et al., "Blockade of the B7-CD28 Pathway by CTLA4-Ig Counteracts Rejection and Prolongs Survival in Small Bowel Transplantation," Scandinavian Journal of Immunology, 2000, vol. 51 (3), pp. 224-230.

Leonard W.J., et al., "Cytokine Receptor Signaling Pathways," Journal of Allergy and Clinical Immunology, 2000, vol. 105 (5), pp. 877-888.

Liu Y., et al., "Mice with Type 2 and 3 Gaucher Disease Point Mutations Generated By a Single Insertion Mutagenesis Procedure," Proceedings of the National Academy of Sciences, United States of America, 1998, vol. 95 (5), pp. 2503-2508.

Marinova-Mutafchieva L, et al., "A Comparative Study into the Mechanisms of Action of Anti-Tumor Necrosis Factor Alpha, Anti-Cd4, and Combined Anti-Tumor Necrosis Factor Alpha/Anti-Cd4 Treatment in Early Collagen-Induced Arthritis," Arthritis & Rheumatology, 2000, vol. 43 (3), pp. 638-644.

Mistry P.K., et al., "A Practical Approach to Diagnosis and Management of Gaucher's Disease," Baillieres Clinical Haematology, 1997, vol. 10 (4), pp. 817-838.

Moder K.G., "New Medications for Use in Patients with Rheumatoid Arthritis," Annals of Allergy, Asthma & Immunology, 2000, vol. 84 (3), pp. 280-284.

Morales L.E., "Gaucher's Disease: A Review," Annals of Pharmacotherapy, 1996, vol. 30 (4), pp. 381-388.

Nevins T.E., "Overview of New Immunosuppressive Therapies," Current Opinion in Pediatrics, 2000, vol. 12 (2), pp. 146-150.

Nilsson O., et al., "Accumulation of Glucosylceramide and Glucosylsphingosine (Psychosine) in Cerebrum and Cerebellum in Infantile and Juvenile Gaucher Disease," Journal of Neurochemistry, 1982, vol. 39 (3), pp. 709-718.

Oberholzer A, et al., "Cytokine Signaling—Regulation of the Immune Response in Normal and Critically ill States," Critical Care Medicine, 2000, vol. 28 (Suppl 4), pp. N3-N12.

Pastores G.M., et al., "Enzyme Therapy in Gaucher Disease Type 1: Dosage Efficacy and Adverse Effects in 33 Patients Treated for 6 to 24 Months," Blood, 1993, vol. 82 (2), pp. 408-416.

Ponticelli C., et al., "Promising New Agents in the Prevention of Transplant Rejection," Drugs in R and D, 1999, vol. 1 (1), pp. 55-60.

Potter M.A., et al., "Review—The Use of Immunosuppressive Agents to Prevent Neutralizing Antibodies against a Transgene Product," Annals of the New York Academy of Sciences, 1999, vol. 875, pp. 159-174.

Przepiorka D., et al., "A Phase II Study of BTI-322, a Monoclonal Anti-CD2 Antibody, for Treatment of Steroid-Resistant Acute Graft-Versus-Host Disease," Blood, 1998, vol. 92 (11), pp. 4066-4071.

Qi S., et al., "Effect of Tacrolimus (FK506) and Sirolimus (rapamycin) Mono- and Combination Therapy in Prolongation of Renal Allograft Survival in the Monkey," Transplantation, 2000, vol. 69 (7), pp. 1275-1283.

Rosenthal D.I., et al., "Enzyme Replacement Therapy for Gaucher Disease: Skeletal Responses to Macrophage-Targeted Glucocerebrosidase," Pediatrics, 1995, vol. 96 (4 Pt 1), pp. 629-637.

Rubinstein M., et al., "Recent Advances in Cytokines, Cytokine Receptors and Signal Transduction," Cytokine & Growth Factor Reviews, 1998, vol. 9 (2), pp. 175-181.

Ryan E.A., et al., "Clinical Outcomes and Insulin Secretion after Islet Transplantation with the Edmonton Protocol," Diabetes, 2001, vol. 50 (4), pp. pp. 710-719.

Shapiro A.M., et al., "Islet Transplantation in Seven Patients with Type 1 Diabetes Mellitus Using a Glucocorticoid-Free Immunosuppressive Regimen," The New England Journal of Medicine, 2000, vol. 343 (4), pp. 230-238.

Slavik J.M., et al., "CD28/CTLA-4 and CD80/CD86 Families: Signaling and Function," Immunologic Research, 1999, vol. 19 (1), pp. 1-24.

Treiber A., et al., "The Pharmacokinetics and Tissue Distribution of the Glucosylceramide Synthase Inhibitor Miglustat in the Rat," Xenobiotica, vol. 37 (3), pp. 298-314.

Turzanski J., et al., "P-Glycoprotein Is Implicated In the Inhibition of Ceramide-Induced Apoptosis in Tf-1 Acute Mlyeloid Leukemia Cells by Modulation of The Glucosylceramide Synthase Pathwa," Experimental Hematology, 2005, 33 (1), pp. 62-72.

Weinreb N.J., et al., "Effectiveness of Enzyme Replacement Therapy in 1028 Patients with Type 1 Gaucher Disease after 2 to 5 Years of Treatment: A Report from the Gaucher Registry," The American Journal of Medicine, 2002, vol. 113 (2), pp. 112-119.

Wiseman L.R., et al., "Daclizumab: A Review of its use in the Prevention of Acute Rejection in Renal Transplant Recipients," Drugs, 1999, vol. 58 (6), pp. 1029-1042.

Yamashita T., et al., "A Vital Role for Glycosphingolipid Synthesis during Development and Differentiation," Proceedings of the National Academy of Sciences, United States of America, 1999, vol. 96 (16), pp. 9142-9147.

Young E., et al., "Plasma Chitotriosidase Activity in Gaucher Disease Patients Who Have Been Treated either by Bone Marrow Transplantation or by Enzyme Replacement Therapy with Alglucerase," Journal of Inherited Metabolic Disease, 1997, vol. 20 (4), pp. 595-602.

* cited by examiner

SALT FORMS OF (S)-QUINUCLIDIN-3-YL (2-(2-(4-FLUOROPHENYL)THIAZOL-4-YL) PROPAN-2-YL)CARBAMATE

CROSS REFERENCE TO RELATED APPLICATION

This application is a 371 National Phase Entry application of co-pending International Application No. PCT/US2014/027081, filed Mar. 14, 2014, which claims the benefit under 35 U.S.C. §119 of U.S. Provisional Application 61/791,706, filed Mar. 15, 2013, all of which are hereby incorporated by reference in their entirety.

BACKGROUND OF THE INVENTION

The present invention relates to novel salt forms of (S)-Quinuclidin-3-yl (2-(2-(4-fluorophenyl)thiazol-4-yl) propan-2-yl)carbamate useful as an inhibitor of glucosylceramide synthase (GCS) and for the treatment metabolic diseases, such as lysosomal storage diseases, either alone or in combination with enzyme replacement therapy, and for the treatment of cancer.

Glucosylceramide synthase (GCS) is a pivotal enzyme which catalyzes the initial glycosylation step in the biosynthesis of glucosylceramide-base glycosphingolipids (GSLs) namely via the pivotal transfer of glucose from UDP-glucose (UDP-Glc) to ceramide to form glucosylceramide. GCS is a transmembrane, type III integral protein localized in the cis/medial Golgi. Glycosphingolipids (GSLs) are believed to be integral for the dynamics of many cell membrane events, including cellular interactions, signaling and trafficking. Synthesis of GSL structures has been shown (see, Yamashita et al., Proc. Natl. Acad. Sci. USA 1999, 96(16), 9142-9147) to be essential for embryonic development and for the differentiation of some tissues. Ceramide plays a central role in sphingolipid metabolism and down-regulation of GCS activity has been shown to have marked effects on the sphingolipid pattern with diminished expression of glycosphingolipids. Sphingolipids (SLs) have a biomodulatory role in physiological as well as pathological cardiovascular conditions. In particular, sphingolipids and their regulating enzymes appear to play a role in adaptive responses to chronic hypoxia in the neonatal rat heart (see, El Alwanit et al., Prostaglandins & Other Lipid Mediators 2005, 78(1-4), 249-263).

GCS inhibitors have been proposed for the treatment of a variety of diseases (see for example, WO2005068426). Such treatments include treatment of glycolipid storage diseases (e.g., Tay Sachs, Sandhoffs, GM2 Activator deficiency, GM1 gangliosidosis and Fabry diseases), diseases associated with glycolipid accumulation (e.g., Gaucher disease; Miglustat (Zavesca), a GCS inhibitor, has been approved for therapy in type 1 Gaucher disease patients, see, Treiber et al., Xenobiotica 2007, 37(3), 298-314), diseases that cause renal hypertrophy or hyperplasia such as diabetic nephropathy; diseases that cause hyperglycemia or hyperinsulemia; cancers in which glycolipid synthesis is abnormal, infectious diseases caused by organisms which use cell surface glycolipids as receptors, infectious diseases in which synthesis of glucosylceramide is essential or important, diseases in which synthesis of glucosylceramide is essential or important, diseases in which excessive glycolipid synthesis occurs (e.g., atherosclerosis, polycystic kidney disease, and renal hypertrophy), neuronal disorders, neuronal injury, inflammatory diseases or disorders associated with macrophage recruitment and activation (e.g., rheumatoid arthritis, Crohn's disease, asthma and sepsis) and diabetes mellitus and obesity (see, WO 2006053043).

In particular, it has been shown that overexpression of GCS is implicated in multi-drug resistance and disrupts ceramide-induced apoptosis. For example, Turzanski et al., (Experimental Hematology 2005, 33 (1), 62-72 have shown that ceramide induces apoptosis in acute myeloid leukemia (AML) cells and that P-glycoprotein (p-gp) confers resistance to ceramide-induced apoptosis, with modulation of the ceramide-glucosylceramide pathway making a marked contribution to this resistance in TF-1 cells. Thus, GCS inhibitors can be useful for treatment of proliferative disorders by inducing apoptosis in diseased cells.

SUMMARY OF THE INVENTION

The present invention relates to a crystalline Form A of (S)-Quinuclidin-3-yl (2-(2-(4-fluorophenyl)thiazol-4-yl) propan-2-yl)carbamate malate, wherein said x-ray powder diffraction contains the following 2-theta peak measured using CuK$_\alpha$ radiation: 18.095.

The present invention further relates to a crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095 and 17.493.

The present invention further relates to a crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095 and 19.516.

The present invention further relates to a crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095, 17.493, and 19.516.

The present invention further relates to a crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095, 17.493, 19.516 and 20.088.

The present invention further relates to a crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095, 17.493, 19.516 and 20.088 and 17.125.

The present invention further relates to a crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peak measured using CuK$_\alpha$ radiation: 24.355.

The present invention further relates to a crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355 and 21.167.

The present invention further relates to a crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355, 21.167 and 27.343.

The present invention further relates to a crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355, 21.167, 27.343 and 16.111.

The present invention further relates to a crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355, 21.167, 27.343, 16.111 and 17.185.

The present invention further relates to a crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355, 21.167, 27.343, 16.111, 17.185 and 20.243.

The present invention further relates to a crystalline form of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peak measured using CuK$_\alpha$ radiation: 17.162.

The present invention further relates to a crystalline Form A of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162 and 18.028.

The present invention further relates to a crystalline Form A of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162 and 14.280.

The present invention further relates to a crystalline Form A of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162, 18.028 and 14.280.

The present invention further relates to a crystalline Form A of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162, 18.028, 14.280 and 18.153.

The present invention further relates to a crystalline Form A of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162, 18.028, 14.280, 18.153 and 23.422.

The present invention further relates to a crystalline form of (S)-Quinuclidin-3-yl (2-(2-(4-fluorophenyl)thiazol-4-yl)propan-2-yl)carbamate HCl salt, wherein said x-ray powder diffraction contains the following 2-theta peak measured using CuK$_\alpha$ radiation: 18.087.

The present invention further relates to a crystalline Form A of (S)-Quinuclidin-3-yl (2-(2-(4-fluorophenyl)thiazol-4-yl)propan-2-yl)carbamate HCl salt, wherein said x-ray powder diffraction contains the following 2-theta peak measured using CuK$_\alpha$ radiation: 12.818.

The present invention further relates to a crystalline Form A of (S)-Quinuclidin-3-yl (2-(2-(4-fluorophenyl)thiazol-4-yl)propan-2-yl)carbamate HCl salt, wherein said x-ray powder diffraction contains the following 2-theta peak measured using CuK$_\alpha$ radiation: 25.722.

The present invention further relates to a crystalline Form A of (S)-Quinuclidin-3-yl (2-(2-(4-fluorophenyl)thiazol-4-yl)propan-2-yl)carbamate HCl salt, wherein said x-ray powder diffraction contains the following 2-theta peaks measured using CuK$_\alpha$ radiation: 12.818 and 25.722.

The present invention further relates to a crystalline Form A of (S)-Quinuclidin-3-yl (2-(2-(4-fluorophenyl)thiazol-4-yl)propan-2-yl)carbamate HCl salt, wherein said x-ray powder diffraction contains the following 2-theta peaks measured using CuK$_\alpha$ radiation: 12.818, 25.722 and 13.040.

The present invention further relates to a crystalline Form A of (S)-Quinuclidin-3-yl (2-(2-(4-fluorophenyl)thiazol-4-yl)propan-2-yl)carbamate HCl salt, wherein said x-ray powder diffraction contains the following 2-theta peaks measured using CuK$_\alpha$ radiation: 12.818, 25.722, 13.040 and 28.910.

Figure 1:
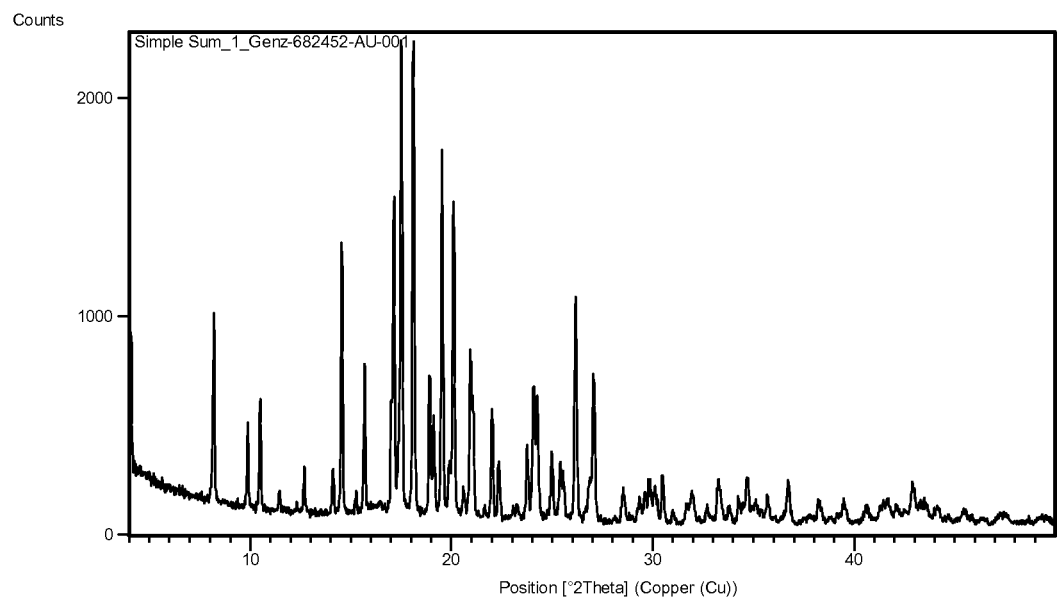
FIG. 1

Diffractogram of crystalline Form A of (S)-Quinuclidin-3-yl (2-(2-(4-fluorophenyl)thiazol-4-yl)propan-2-yl)carbamate malate carried out on a Bruker D8-Advance diffractometer.

FIG. 2

Diffractogram of crystalline Form B of (S)-Quinuclidin-3-yl (2-(2-(4-fluorophenyl)thiazol-4-yl)propan-2-yl)carbamate malate carried out on a Bruker D8-Advance diffractometer.

FIG. 3

Diffractogram of crystalline (S)-Quinuclidin-3-yl (2-(2-(4-fluorophenyl)thiazol-4-yl)propan-2-yl)carbamate (S)-2-hydroxysuccinate salt carried out on a Bruker D8-Advance diffractometer.

FIG. 4

Diffractogram of crystalline form of (S)-Quinuclidin-3-yl (2-(2-(4-fluorophenyl)thiazol-4-yl)propan-2-yl)carbamate HCl salt carried out on a Bruker D8-Advance diffractometer.

DETAILED DESCRIPTION OF THE INVENTION

The first aspect of the invention is directed to crystalline Form A of (S)-Quinuclidin-3-yl (2-(2-(4-fluorophenyl)thiazol-4-yl)propan-2-yl)carbamate malate characterized by the following x-ray powder diffraction pattern expressed in terms of the 2-theta and relative intensities with a relative intensity of >0.52% (Table 1) The measurements were conducted as follows: Apparatus: Bruker D8-Advance diffractometer, type: Bragg-Brentano; Source CuK$_\alpha$1, wavelength=1.5406 Å; Generator: 35 kV-40 mA; Detector: PSD/Vantec; Anton Paar TTK450 chamber; Si sample holder; Angle range: 2° to 40° in 2-theta Bragg; Variable Divergence Slit: 4 mm (V4); Step size: 0.033°; Step time: 1 s.

TABLE 1

In order of 2theta position and d-spacing

| No. | Pos. [°2Th.] | d-spacing [Å] | Rel. Int. [%] |
|---|---|---|---|
| 1 | 7.918 | 11.1570 | 9.55 |
| 2 | 10.255 | 8.6186 | 7.36 |
| 3 | 11.633 | 7.6007 | 14.27 |
| 4 | 14.049 | 6.2987 | 28.16 |
| 5 | 14.280 | 6.1973 | 45.27 |
| 6 | 15.868 | 5.5807 | 4.69 |
| 7 | 17.162 | 5.1627 | 100 |
| 8 | 18.028 | 4.9165 | 46.12 |
| 9 | 18.153 | 4.8829 | 43.86 |

TABLE 1-continued

In order of 2theta position and d-spacing

| No. | Pos. [°2Th.] | d-spacing [Å] | Rel. Int. [%] |
|---|---|---|---|
| 10 | 19.688 | 4.5055 | 13.34 |
| 11 | 19.878 | 4.4630 | 24.63 |
| 12 | 20.308 | 4.3693 | 5.01 |
| 13 | 20.449 | 4.3395 | 13.21 |
| 14 | 20.617 | 4.3046 | 19.14 |
| 15 | 21.079 | 4.2112 | 14.8 |
| 16 | 21.691 | 4.0938 | 3.3 |
| 17 | 21.981 | 4.0404 | 6.56 |
| 18 | 22.203 | 4.0006 | 9.02 |
| 19 | 23.422 | 3.7951 | 42.99 |
| 20 | 23.794 | 3.7365 | 2.73 |
| 21 | 24.273 | 3.6639 | 7 |
| 22 | 24.740 | 3.5955 | 7.35 |
| 23 | 24.896 | 3.5736 | 7.91 |
| 24 | 25.016 | 3.5567 | 7.44 |
| 25 | 25.759 | 3.4558 | 8 |
| 26 | 25.998 | 3.4246 | 3.56 |
| 27 | 27.250 | 3.2700 | 22.05 |
| 28 | 27.799 | 3.2067 | 2.92 |
| 29 | 28.350 | 3.1455 | 5.19 |
| 30 | 28.815 | 3.0959 | 6.25 |
| 31 | 29.229 | 3.0530 | 2.5 |
| 32 | 29.602 | 3.0153 | 6.24 |
| 33 | 30.163 | 2.9605 | 5.52 |
| 34 | 30.729 | 2.9073 | 2.14 |
| 35 | 31.153 | 2.8686 | 4.18 |
| 36 | 31.380 | 2.8486 | 2.6 |
| 37 | 31.630 | 2.8266 | 1.92 |
| 38 | 31.916 | 2.8018 | 2.66 |
| 39 | 32.100 | 2.7861 | 1.4 |
| 40 | 32.767 | 2.7309 | 1.31 |
| 41 | 33.730 | 2.6548 | 1.18 |
| 42 | 34.333 | 2.6099 | 3.32 |
| 43 | 34.620 | 2.5889 | 2.46 |
| 44 | 34.880 | 2.5699 | 4.51 |
| 45 | 35.090 | 2.5553 | 4.58 |
| 46 | 35.437 | 2.5310 | 2.41 |
| 47 | 36.420 | 2.4649 | 0.78 |
| 48 | 36.800 | 2.4376 | 0.29 |
| 49 | 37.000 | 2.4364 | 0.87 |
| 50 | 38.330 | 2.3465 | 1.15 |
| 51 | 38.680 | 2.3262 | 0.97 |
| 52 | 38.990 | 2.3083 | 1.27 |
| 53 | 39.940 | 2.2553 | 1.26 |
| 54 | 40.385 | 2.2316 | 1.95 |
| 55 | 40.960 | 2.2016 | 1.41 |

The second aspect of the invention is directed to crystalline Form B of (S)-Quinuclidin-3-yl (2-(2-(4-fluorophenyl)thiazol-4-yl)propan-2-yl)carbamate malate characterized by the following x-ray powder diffraction pattern expressed in terms of the 2-theta and relative intensities with a relative intensity of >8% (Table 2). The measurements were conducted as follows: Apparatus: Bruker D8-Advance diffractometer, type: Bragg-Brentano; Source CuK$_\alpha$1, wavelength=1.5406 Å; Generator: 35 kV-40 mA; Detector: PSD/Vantec; Anton Paar TTK450 chamber; Si sample holder; Angle range: 2° to 40° in 2-theta Bragg; Variable Divergence Slit: 4 mm (V4); Step size: 0.033°; Step time: 1 s.

TABLE 2

| Angle-2 Theta° | Relative Intensity % |
|---|---|
| 3.957 | 15.7 |
| 7.981 | 32.0 |
| 10.508 | 10.5 |
| 12.768 | 17.7 |
| 14.195 | 23.3 |
| 14.570 | 28.5 |
| 16.111 | 53.7 |
| 16.982 | 13.5 |
| 17.185 | 46.0 |
| 17.691 | 11.6 |
| 18.744 | 10.6 |
| 19.055 | 22.9 |
| 19.315 | 10.0 |
| 19.454 | 12.8 |
| 20.243 | 41.3 |
| 20.722 | 13.7 |
| 21.167 | 86.1 |
| 21.516 | 11.4 |
| 21.610 | 11.3 |
| 22.466 | 20.3 |
| 23.626 | 16.6 |
| 23.765 | 21.5 |
| 24.097 | 20.2 |
| 24.355 | 100.0 |
| 24.823 | 10.0 |
| 25.243 | 13.4 |
| 25.337 | 13.9 |
| 25.637 | 18.2 |
| 25.809 | 12.2 |
| 26.681 | 15.7 |
| 26.801 | 18.9 |
| 27.343 | 57.6 |
| 27.765 | 12.3 |
| 28.670 | 12.1 |
| 28.861 | 17.6 |
| 29.516 | 34.8 |
| 30.745 | 12.8 |
| 31.285 | 14.3 |
| 31.470 | 15.5 |
| 31.803 | 18.1 |
| 32.023 | 15.2 |
| 32.151 | 14.7 |
| 32.491 | 15.7 |
| 32.609 | 15.9 |
| 33.303 | 15.3 |
| 33.520 | 14.1 |
| 33.791 | 16.9 |
| 34.101 | 15.7 |
| 34.219 | 17.4 |
| 34.380 | 18.7 |
| 34.460 | 18.9 |
| 34.942 | 24.6 |
| 35.566 | 13.9 |
| 35.730 | 14.0 |
| 35.965 | 14.7 |
| 36.913 | 16.2 |
| 37.712 | 14.0 |
| 38.120 | 16.5 |
| 38.268 | 17.7 |
| 38.731 | 18.7 |
| 39.042 | 16.5 |
| 39.257 | 16.4 |

The third aspect of the invention is directed to crystalline form of (S)-Quinuclidin-3-yl (2-(2-(4-fluorophenyl)thiazol-4-yl)propan-2-yl)carbamate (S)-2-hydroxysuccinate salt characterized by the following x-ray powder diffraction pattern expressed in terms of the 2-theta and relative intensities with a relative intensity of >8% (Table 3). The measurements were conducted as follows: Apparatus: Bruker D8-Advance diffractometer, type: Bragg-Brentano; Source CuK$_\alpha$1, wavelength=1.5406 Å; Generator: 35 kV-40 mA; Detector: PSD/Vantec; Anton Paar TTK450 chamber; Si sample holder; Angle range: 2° to 40° in 2-theta Bragg; Variable Divergence Slit: 4 mm (V4); Step size: 0.033°; Step time: 1 s.

TABLE 3

In order of 2-theta position and d-spacing

| No. | Pos. [°2Th.] | d-spacing [Å] | Rel. Int. [%] |
|---|---|---|---|
| 1 | 7.918 | 11.1570 | 9.55 |
| 2 | 10.255 | 8.6186 | 7.36 |
| 3 | 11.633 | 7.6007 | 14.27 |
| 4 | 14.049 | 6.2987 | 28.16 |
| 5 | 14.280 | 6.1973 | 45.27 |
| 6 | 15.868 | 5.5807 | 4.69 |
| 7 | 17.162 | 5.1627 | 100 |
| 8 | 18.028 | 4.9165 | 46.12 |
| 9 | 18.153 | 4.8829 | 43.86 |
| 10 | 19.688 | 4.5055 | 13.34 |
| 11 | 19.878 | 4.4630 | 24.63 |
| 12 | 20.308 | 4.3693 | 5.01 |
| 13 | 20.449 | 4.3395 | 13.21 |
| 14 | 20.617 | 4.3046 | 19.14 |
| 15 | 21.079 | 4.2112 | 14.8 |
| 16 | 21.691 | 4.0938 | 3.3 |
| 17 | 21.981 | 4.0404 | 6.56 |
| 18 | 22.203 | 4.0006 | 9.02 |
| 19 | 23.422 | 3.7951 | 42.99 |
| 20 | 23.794 | 3.7365 | 2.73 |
| 21 | 24.273 | 3.6639 | 7 |
| 22 | 24.740 | 3.5955 | 7.35 |
| 23 | 24.896 | 3.5736 | 7.91 |
| 24 | 25.016 | 3.5567 | 7.44 |
| 25 | 25.759 | 3.4558 | 8 |
| 26 | 25.998 | 3.4246 | 3.56 |
| 27 | 27.250 | 3.2700 | 22.05 |
| 28 | 27.799 | 3.2067 | 2.92 |
| 29 | 28.350 | 3.1455 | 5.19 |
| 30 | 28.815 | 3.0959 | 6.25 |
| 31 | 29.229 | 3.0530 | 2.5 |
| 32 | 29.602 | 3.0153 | 6.24 |
| 33 | 30.163 | 2.9605 | 5.52 |
| 34 | 30.729 | 2.9073 | 2.14 |
| 35 | 31.153 | 2.8686 | 4.18 |
| 36 | 31.380 | 2.8486 | 2.6 |
| 37 | 31.630 | 2.8266 | 1.92 |
| 38 | 31.916 | 2.8018 | 2.66 |
| 39 | 32.100 | 2.7861 | 1.4 |
| 40 | 32.767 | 2.7309 | 1.31 |
| 41 | 33.730 | 2.6548 | 1.18 |
| 42 | 34.333 | 2.6099 | 3.32 |
| 43 | 34.620 | 2.5889 | 2.46 |
| 44 | 34.880 | 2.5699 | 4.51 |
| 45 | 35.090 | 2.5553 | 4.58 |
| 46 | 35.437 | 2.5310 | 2.41 |
| 47 | 36.420 | 2.4649 | 0.78 |
| 48 | 36.800 | 2.4376 | 0.29 |
| 49 | 37.000 | 2.4364 | 0.87 |
| 50 | 38.330 | 2.3465 | 1.15 |
| 51 | 38.680 | 2.3262 | 0.97 |
| 52 | 38.990 | 2.3083 | 1.27 |
| 53 | 39.940 | 2.2553 | 1.26 |
| 54 | 40.385 | 2.2316 | 1.95 |
| 55 | 40.960 | 2.2016 | 1.41 |

The fourth aspect of the invention is directed to a crystalline form of (S)-Quinuclidin-3-yl (2-(2-(4-fluorophenyl)thiazol-4-yl)propan-2-yl)carbamate HCl salt characterized by the following x-ray powder diffraction pattern expressed in terms of the 2-theta and relative intensities with a relative intensity of >0.96% (Table 4). The measurements were conducted as follows: Apparatus: Bruker D8-Advance diffractometer, type: Bragg-Brentano; Source CuK$_\alpha$1, wavelength=1.5406 Å; Generator: 35 kV-40 mA; Detector: PSD/Vantec; Anton Paar TTK450 chamber; Si sample holder; Angle range: 2° to 40° in 2-theta Bragg; Variable Divergence Slit: 4 mm (V4); Step size: 0.033°; Step time: 1 s.

TABLE 4

In order of 2theta position and d-spacing

| No. | Pos. [°2Th.] | d-spacing [Å] | Rel. Int. [%] |
|---|---|---|---|
| 1 | 12.818 | 6.9008 | 50.54 |
| 2 | 13.040 | 6.7842 | 18.21 |
| 3 | 13.378 | 6.6147 | 3.89 |
| 4 | 13.829 | 6.3987 | 10.68 |
| 5 | 14.124 | 6.2658 | 7.61 |
| 6 | 14.384 | 6.1532 | 6.98 |
| 7 | 14.893 | 5.9441 | 2.95 |
| 8 | 15.060 | 5.8785 | 12.79 |
| 9 | 15.338 | 5.7725 | 1.11 |
| 10 | 15.827 | 5.5952 | 5.17 |
| 11 | 16.069 | 5.5114 | 4.36 |
| 12 | 16.679 | 5.3113 | 10.92 |
| 13 | 17.577 | 5.0416 | 17.64 |
| 14 | 18.087 | 4.9007 | 100 |
| 15 | 18.474 | 4.8008 | 6.95 |
| 16 | 18.865 | 4.7002 | 2.58 |
| 17 | 19.321 | 4.5903 | 1.34 |
| 18 | 19.840 | 4.4715 | 2.00 |
| 19 | 20.441 | 4.3412 | 4.64 |
| 20 | 21.050 | 4.2170 | 2.59 |
| 21 | 21.720 | 4.0883 | 0.96 |
| 22 | 22.784 | 3.8999 | 2.32 |
| 23 | 23.415 | 3.7961 | 0.97 |
| 24 | 23.923 | 3.7166 | 3.31 |
| 25 | 24.214 | 3.6727 | 2.51 |
| 26 | 24.619 | 3.6132 | 3.23 |
| 27 | 25.106 | 3.5441 | 2.09 |
| 28 | 25.722 | 3.4607 | 31.45 |
| 29 | 26.064 | 3.4161 | 8.72 |
| 30 | 26.241 | 3.3933 | 3.55 |
| 31 | 26.978 | 3.3023 | 3.92 |
| 32 | 27.217 | 3.2739 | 2.61 |
| 33 | 27.895 | 3.1958 | 1.75 |
| 34 | 28.460 | 3.1337 | 2.86 |
| 35 | 28.910 | 3.0859 | 18.11 |
| 36 | 29.934 | 2.9826 | 4.41 |
| 37 | 30.374 | 2.9410 | 1.45 |
| 38 | 30.774 | 2.9030 | 1.03 |
| 39 | 31.245 | 2.8604 | 3.25 |
| 40 | 31.883 | 2.8046 | 1.24 |
| 41 | 32.484 | 2.7540 | 0.79 |
| 42 | 33.104 | 2.7042 | 0.86 |
| 43 | 33.810 | 2.6490 | 1.77 |
| 44 | 35.069 | 2.5568 | 0.61 |
| 45 | 35.526 | 2.5270 | 1.09 |
| 46 | 36.243 | 2.4766 | 0.52 |
| 47 | 36.721 | 2.4475 | 1.20 |
| 48 | 39.164 | 2.3003 | 0.83 |

Several approaches are being used or pursued for the treatment of LSDs, most of which focus on enzyme replacement therapy for use alone in disease management. Numerous approved enzyme replacement therapies are commercially available for treating LSDs (e.g., Myozyme® for Pompe disease, Aldurazyme® for Mucopolysaccharidosis I, Cerezyme® for Gaucher disease and Fabrazyme® for Fabry disease). Additionally, the inventors have identified a number of small molecules for use alone in the management of LSDs. The therapeutic methods of the invention described herein provide treatment options for the practitioner faced with management of various lysosomal storage diseases, as described in detail below.

In certain aspects of the invention, the compounds of the present invention may be used to treat a metabolic disease, such as a lysosomal storage disease (LSD), either alone or as a combination therapy with an enzyme replacement therapy. In other aspects of the invention, the compounds of the present invention may be used to inhibit or reduce GCS activity in a subject diagnosed with a metabolic disease, such as an LSD, either alone or as a combination therapy with an enzyme replacement therapy. In other aspects of the invention, the compounds of the present invention may be used to reduce and/or inhibit the accumulation of a stored material (e.g., lysosomal substrate) in a subject diagnosed with a metabolic disease, such as an LSD. In certain embodiments of the foregoing aspects, the LSD is Gaucher (type 1, type 2 or type 3), Fabry, $G_{M1}$-gangliosidosis or $G_{M2}$-gangliosidoses (e.g., GM2 Activator Deficiency, Tay-Sachs and Sandhoff). Table 1 lists numerous LSDs and identifies the corresponding deficient enzyme that may be used as an ERT in the foregoing aspects of the invention.

In other scenarios it may be necessary to provide SMT to a patient whose condition requires the reduction of substrates in the brain and thus is not treatable by systemic administration of ERT. While direct intracerebroventricular or intathecal administration can reduce substrate levels in the brain, systemic administration of ERT is not amenable for LSD's with Central Nervous System (CNS) involvement due to its incapacity to cross the Blood Brain Barrier (BBB) and SMT may prove beneficial in patients having residual enzymatic activities in the CNS.

In accordance with the present invention, SMT is provided to a patient to treat a cancer and/or metabolic disease, such as, a lysosomal storage disease. The SMT may include one or more small molecules. The SMT includes administering to the patient compounds of the present invention. In particular embodiments, the compound is (S)-Quinuclidin-3-yl (2-(2-(4-fluorophenyl)thiazol-4-yl)propan-2-yl)carbamate or Quinuclidin-3-yl (2-(4'-fluoro-[1,1'-biphenyl]-3-yl)propan-2-yl)carbamate, or combinations thereof.

In certain embodiments, compounds of the invention, such as, for example, (S)-Quinuclidin-3-yl (2-(2-(4-fluorophenyl)thiazol-4-yl)propan-2-yl)carbamate and Quinuclidin-3-yl (2-(4'-fluoro-[1,1'-biphenyl]-3-yl)propan-2-yl)carbamate may be used for treatment of virtually any storage disease resulting from a defect in the glycosphingolipid pathway (e.g. Gaucher (i.e., type 1, type 2 type 3), Fabry, $G_{M1}$-gangliosidosis, $G_{M2}$-gangliosidoses (e.g., GM2 Activator Deficiency, Tay-Sachs and Sandhoff)). In a particularly preferred embodiment, (S)-Quinuclidin-3-yl (2-(2-(4-fluorophenyl)thiazol-4-yl)propan-2-yl)carbamate or a pharmaceutically acceptable salt or prodrug thereof is used to inhibit and/or reduce the accumulation of Gb3 and/or lyso-Gb3 in a patient with Fabry disease, either alone or as a combination therapy with enzyme replacement therapy (see Examples). In a preferred embodiment, the enzyme replacement therapy includes administering alpha-galactosidase A to the Fabry patient. Indeed, the Examples below demonstrate that a GCS inhibitor of the invention effectively reduces Gb3 and lyso-Gb3 storage in a mouse model of Fabry disease, thus supporting its use as a viable approach for the treatment of Fabry disease. Furthermore, in vivo combination therapy data provided in the Examples strongly suggest that a combined therapeutic approach could be both additive and complementary.

In certain embodiments, compounds of the invention, such as, for example, (S)-Quinuclidin-3-yl (2-(2-(4-fluorophenyl)thiazol-4-yl)propan-2-yl)carbamate and Quinuclidin-3-yl (2-(4'-fluoro-[1,1'-biphenyl]-3-yl)propan-2-yl)carbamate may be used for reducing the level of GluCer and GluSph in the brain of a subject diagnosed with neuropathic Gaucher disease, either alone or in combination with ERT (e.g., glucocerebrosidase administration).

Dosage regimens for a small molecule therapy component of a combination therapy of the invention are generally determined by the skilled clinician and are expected to vary significantly depending on the particular storage disease being treated and the clinical status of the particular affected individual. The general principles for determining a dosage regimen for a given SMT of the invention for the treatment of any storage disease are well known to the skilled artisan. Guidance for dosage regimens can be obtained from any of the many well known references in the art on this topic. Further guidance is available, inter alia, from a review of the specific references cited herein. In certain embodiments, such dosages may range from about 0.5 mg/kg to about 300 mg/kg, preferably from about 5 mg/kg to about 60 mg/kg (e.g., 5 mg/kg, 10 mg/kg, 15, mg/kg, 20 mg/kg, 25 mg/kg, 30 mg/kg, 35 mg/kg, 40 mg/kg, 45 mg/kg, 50 mg/kg, 55 mg/kg and 60 mg/kg) by intraperitoneal, oral or equivalent administration from one to five times daily. Such dosages may range from about 5 mg/kg to about 5 g/kg, preferably from about 10 mg/kg to about 1 g/kg by oral, intraperitoneal or equivalent administration from one to five times daily. In one embodiment, doses range from about about 10 mg/day to about 500 mg/day (e.g., 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 mg/day, 240 mg/day, 250 mg/day, 260 mg/day, 270 mg/day, 280 mg/day, 290 mg/day, 300 mg/day). A particularly preferred oral dose range is from about 50 mg to about 100 mg, wherein the dose is administered twice daily. A particular oral dose range for a compound of the present invention is from about 5 mg/kg/day to about 600 mg/kg/day. In a particular oral dose range for a compound of the present invention is from about 1 mg/kg/day to about 120 mg/kg/day, e.g., 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day or 60 mg/kg/day, 65 mg/kg/day, 70 mg/kg/day, 75 mg/kg/day, 80 mg/kg/day, 85 mg/kg/day, 90 mg/kg/day, 95 mg/kg/day, 100 mg/kg/day, 105 mg/kg/day, 110 mg/kg/day, 115 mg/kg/day or 120 mg/kg/day.

In certain embodiments, the invention relates to combination therapies of SMT using compounds of the invention and ERT therapy for the treatment of lysosomal storage diseases. A partial list of known lysosomal storage diseases that can be treated in accordance with the invention is set forth in Table 5, including common disease name, material stored, and corresponding enzyme deficiency (adapted from Table 38-4 of Kolodny et al., 1998, Id.).

TABLE 5

Lysosomal Storage Diseases

| Disease | Material Stored | Enzyme Deficiency |
| --- | --- | --- |
| Sphingolipidoses | | |
| Gaucher | Glucocerebroside, glucosylsphingosine | Glucocerebrosidase |
| Niemann-Pick | Sphingomyelin | Sphingomyelinase |
| Niemann-Pick B | Sphingomyelin | Sphingomyelinase |
| Farber | Ceramide | Ceramidase |

TABLE 5-continued

Lysosomal Storage Diseases

| Disease | Material Stored | Enzyme Deficiency |
|---|---|---|
| $G_{M1}$-gangliosidosis | $G_{M1}$-ganglioside, glycoprotein | $G_{M1}$-ganglioside-β-galactosidase |
| $G_{M2}$-gangliosidosis (Sandhoff) | $G_{M2}$-ganglioside, globoside | Hexosaminidase A and B |
| Tay-Sachs | $G_{M2}$-ganglioside | Hexosaminidase A |
| Krabbe | Galactosylceramide | β-Galactocerebrosidase |
| Mucopolysaccharidoses | | |
| Hurler-Scheie (MPS I) | Dermatan sulfate, heparin Sulfate | α-L-iduronidase |
| Hunter (MPS II) | Dermatan sulfate, heparin sulfate | Iduronate sulfatase |
| Sanfilippo (MPS III) | | |
| Type A | Heparan sulfate | Heparan-N-sulfatase |
| Type B | Heparan sulfate | N-acetyl-α-glucosaminidase |
| Type C | Heparan sulfate | Acetyl CoA:α-glucosaminide acetyl-transferase |
| Type D | Heparan sulfate | N-acetyl-α-glucosamine-6-sulfatase |
| Marquio (MPS IV) | | |
| Type A | Keratan sulfate | Galactosamine-6-sulfatase |
| Type B | Keratan sulfate | β-galactosidase |
| Maroteaux-Lamy (MPS VI) | Dermatan sulfate | Galactosamine-4-sulfatase (arylsulfatase B) |
| Sly (MPS VII) | Dermatan sulfate, heparan Sulfate | β-glucuronidase |
| Mucosulfatidosis | Sulfatides, mucopolysaccharides | Arylsulfatase A, B and C, other sulfatases |
| Mucolipidoses | | |
| Sialidoses | Sialyloligosaccharides, glycoproteins | α-neuraminidase |
| Mucolipidosis II | Sialyloligosaccharides, glycoproteins, glycolipids | High serum, low fibroblast enzymes; N-acetyl-glucosamine-1-phosphate transferase |
| Mucolipidosis III | Glycoproteins, glycolipids | Same as above |
| Mucolipidosis IV | Glycolipids, glycoproteins | Mcoln1 transm protein |
| Other Diseases of Complex Carbohydrate Metabolism | | |
| Fabry | Globotriaosylceramide(Gb3), lyso-Gb3 | α-galactosidase A |
| Schindler | O-linked glycopeptides | α-N-acetylgalactosaminidase |
| Pompe | Glycogen | α-glucosidase |
| Sialic acid storage disease | Free sialic acid | Unknown |
| Fucosidosis | Fucoglycolipids, fucosyloligosaccharides | α-fucosidase |
| Mannosidosis | Mannosyloligosaccharides | α-mannosidase |
| Aspartylglucosaminuria | Aspartylglucosamine | Aspartylglucosamine amidase |
| Wolman | Cholesteryl esters, Triglycerides | Acid lipase |
| Neuronal Ceroid Lipofuscinoses (NCLs)* | | |
| Infintile NCL | Granular osmophilic deposits, Saposins A and D thioesterase | Palmitoyl-protein thioesterase (PPT1) |
| Late Infantile | Curvilinear profiles, ATP synthase subunit c | Tripeptidyl protease 1 (TPP1) |
| Finnish variant | Fingerprint/Rectilinear profiles, ATP synthase subunit c | CLN5 |
| Variant | Fingerprint/Rectilinear profiles, ATP synthase subunit c | CLN6 |
| Juvenile | Fingerprint profile, ATP synthase subunit c | CLN3 |
| Adult | Variable | Unknown |
| Northern Epilepsy | Rectilinear profile, ATP synthase subunit c | CLN8 |
| Turkish variant | Fingerprint/Rectilinear profiles-constituents unknown | Unknown |

TABLE 5-continued

Lysosomal Storage Diseases

| Disease | Material Stored | Enzyme Deficiency |
|---|---|---|
| Lysosomal diseases of cholesterol transport and metabolism | | |
| Niemann-Pick type C | Unesterified cholesterol | NPC1 or NPC2 |

*Davidson et al., The Neuronal Ceroid Lipofuscinosis, Clinical Features and Molecular Basis of Disease. In Barranger J A and Cabrera-Salazar M A (Eds) Lysosomal Storage Disorders. 2007. pp. 371-388. Springer, New York, U.S.A.

Any method known to the skilled artisan may be used to monitor disease status and the effectiveness of a combination therapy of the invention. Clinical monitors of disease status may include but are not limited to organ volume (e.g. liver, spleen), hemoglobin, erythrocyte count, hematocrit, thrombocytopenia, cachexia (wasting), and plasma chitinase levels (e.g. chitotriosidase). Chitotriosidase, an enzyme of the chitinase family, is known to be produced by macrophages in high levels in subjects with lysosomal storage diseases (see Guo et al., 1995, J. Inherit. Metab. Dis. 18, 717-722; den Tandt et al., 1996, J. Inherit. Metab. Dis. 19, 344-350; Dodelson de Kremer et al., 1997, Medicina (Buenos Aires) 57, 677-684; Czartoryska et al., 2000, Clin. Biochem. 33, 147-149; Czartoryska et al., 1998, Clin. Biochem. 31, 417-420; Mistry et al., 1997, Baillieres Clin. Haematol. 10, 817-838; Young et al., 1997, J. Inherit. Metab. Dis. 20, 595-602; Hollak et al., 1994, J. Clin. Invest. 93, 1288-1292). Chitotriosidase is preferably measured in conjuction with angiotensin converting enzyme and non tartrate resistant acid phosphatase to monitor response to treatment of Gaucher patients.

Methods and formulations for administering the combination therapies of the invention include all methods and formulations well known in the art (see, e.g., Remington's Pharmaceutical Sciences, 1980 and subsequent years, 16th ed. and subsequent editions, A. Oslo editor, Easton Pa.; Controlled Drug Delivery, 1987, 2nd rev., Joseph R. Robinson & Vincent H. L. Lee, eds., Marcel Dekker, ISBN: 0824775880; Encyclopedia of Controlled Drug Delivery, 1999, Edith Mathiowitz, John Wiley & Sons, ISBN: 0471148288; U.S. Pat. No. 6,066,626 and references cited therein; see also, references cited in sections below).

According to the invention, the following general approaches are provided for combination therapy in the treatment of lysosomal storage diseases. Each general approach involves combining enzyme replacement therapy with small molecule therapy in a manner consistent with optimizing clinical benefit while minimizing disadvantages associated with using each therapy alone.

In one embodiment of the invention, enzyme replacement therapy (alone or in combination with small molecule therapy) is administered to initiate treatment (i.e., to de-bulk the subject), and small molecule therapy is administered after the de-bulking phase to achieve and maintain a stable, long-term therapeutic effect without the need for frequent intravenous ERT injections. For example, enzyme replacement therapy may be administered intravenously (e.g. over a one to two hour period) once, on a weekly basis, once every two weeks, or once every two months, for several weeks or months, or longer (e.g., until an involved indicator organ such as spleen or liver shows a decrease in size). Moreover, the ERT phase of initial de-bulking treatment can be performed alone or in combination with a small molecule therapy. A small molecule therapeutic component is particularly preferred where the small molecule is compatible with oral administration, thus providing further relief from frequent intravenous intervention.

Alternating among ERT and SMT, or supplementing SMT with ERT as needed, provides a strategy for simultaneously taking advantage of the strengths and addressing the weaknesses associated with each therapy when used alone. An advantage of ERT, whether used for de-bulking and/or for more long-term care, is the much broader clinical experience available to inform the practitioner's decisions. Moreover, a subject can be effectively titrated with ERT during the de-bulking phase by, for example, monitoring biochemical metabolites in urine or other body samples, or by measuring affected organ volume. A disadvantage of ERT, however, is the frequency of the administration required, typically involving intravenous injection on a weekly or bi-weekly basis due to the constant re-accumulation of the substrate. The use of small molecule therapy to reduce the amount of or inhibit substrate accumulation in a patient can in turn reduce the administration frequency of ERT. For example, a bi-weekly enzyme replacement therapy dosing regimen can be offered an "ERT holiday" (e.g., using a SMT) so that frequent enzyme injections are not required therapy. Furthermore, treating a lysosomal storage disease with combination therapy can provide complementary therapeutic approaches. Indeed, as demonstrated in the Examples below, a combination therapy of SMT and ERT can provide significant improvements over either therapeutic platform alone. These data suggest that combination therapy using SMT and ERT can be both additive and complementary. In one embodiment, ERT may be used as a de-bulking strategy (i.e., to initiate treatment), followed by or simultaneously supplemented with SMT using a compound of the present invention. In another embodiment, a patient is first treated with SMT using a compound of the present invention, followed by or simultaneously supplemented with ERT. In other embodiments, a SMT is used to inhibit or reduce further accumulation of substrate (or re-accumulation of substrate if used after debulking with ERT) in a patient with a lysosomal storage disease, and optionally provided ERT as needed to reduce any further substrate accumulation. In one embodiment, this invention provides a method of combination therapy for treatment of a subject diagnosed as having a lysosomal storage disease comprising alternating between administration of an enzyme replacement therapy and a small molecule therapy. In another embodiment, this invention provides a method of combination therapy for treatment of a subject diagnosed as having a lysosomal storage disease comprising simultaneously administering an enzyme replacement therapy and a small molecule therapy. In the various combination therapies of the invention, it will be understood that administering small molecule therapy may occur prior to, concurrently with, or after, administration of enzyme replacement therapy. Similarly, administering enzyme replacement therapy may occur prior to, concurrently with, or after, administration of small molecule therapy.

In any of the embodiments of the invention, the lysosomal storage disease is selected from the group consisting of Gaucher (types 1, 2 and 3), Niemann-Pick, Farber, $G_{M1}$-gangliosidosis, $G_{M2}$-gangliosidoses (e.g., GM2 Activator Deficiency, Tay-Sachs and Sandhoff), Krabbe, Hurler-Scheie (MPS I), Hunter (MPS II), Sanfilippo (MPS III) Type A, Sanfilippo (MPS III) Type B, Sanfilippo (MPS III) Type C, Sanfilippo (MPS III) Type D, Marquio (MPS IV) Type A, Marquio (MPS IV) Type B, Maroteaux-Lamy (MPS VI), Sly (MPS VII), mucosulfatidosis, sialidoses, mucolipidosis II, mucolipidosis III, mucolipidosis IV, Fabry, Schindler, Pompe, sialic acid storage disease, fucosidosis, mannosidosis, aspartylglucosaminuria, Wolman, and neuronal ceroid lipofucsinoses.

Further, the ERT provides an effective amount of at least one of the following enzymes; glucocerebrosidase, sphingomyelinase, ceramidase, $G_{M1}$-ganglioside-beta-galactosidase, hexosaminidase A, hexosaminidase B, beta-galactocerebrosidase, alpha-L-iduronidase, iduronate sulfatase, heparan-N-sulfatase, N-acetyl-alpha-glucosaminidase, acetyl CoA:alpha-glucosaminide acetyl-transferase, N-acetyl-alpha-glucosamine-6-sulfatase, galactosamine-6-sulfatase, beta-galactosidase, galactosamine-4-sulfatase (arylsulfatase B), beta-glucuronidase, arylsulfatase A, arylsulfatase C, alpha-neuraminidase, N-acetyl-glucosamine-1-phosphate transferase, alpha-galactosidase A, alpha-N-acetylgalactosaminidase, alpha-glucosidase, alpha-fucosidase, alpha-mannosidase, aspartylglucosamine amidase, acid lipase, palmitoyl-protein thioesterase (CLN-1), PPT1, TPP1, CLN3, CLNS, CLN6, CLN8, NPC1 or NPC2.

In accordance with the invention, the SMT and/or ERT produce a diminution in at least one of the following stored materials; glucocerebroside, sphingomyelin, ceramide, $G_{M1}$-ganglioside, $G_{M2}$-ganglioside, globoside, galactosylceramide, dermatan sulfate, heparan sulfate, keratan sulfate, sulfatides, mucopolysaccharides, sialyloligosaccharides, glycoproteins, sialyloligosaccharides, glycolipids, globotriaosylceramide, O-linked glycopeptides, glycogen, free sialic acid, fucoglycolipids, fucosyloligosaccharides, mannosyloligosaccharides, aspartylglucosamine, cholesteryl esters, triglycerides, granular osmophilic deposits—Saposins A and D, ATP synthase subunit c, NPC1 or NPC2.

Figure 2:
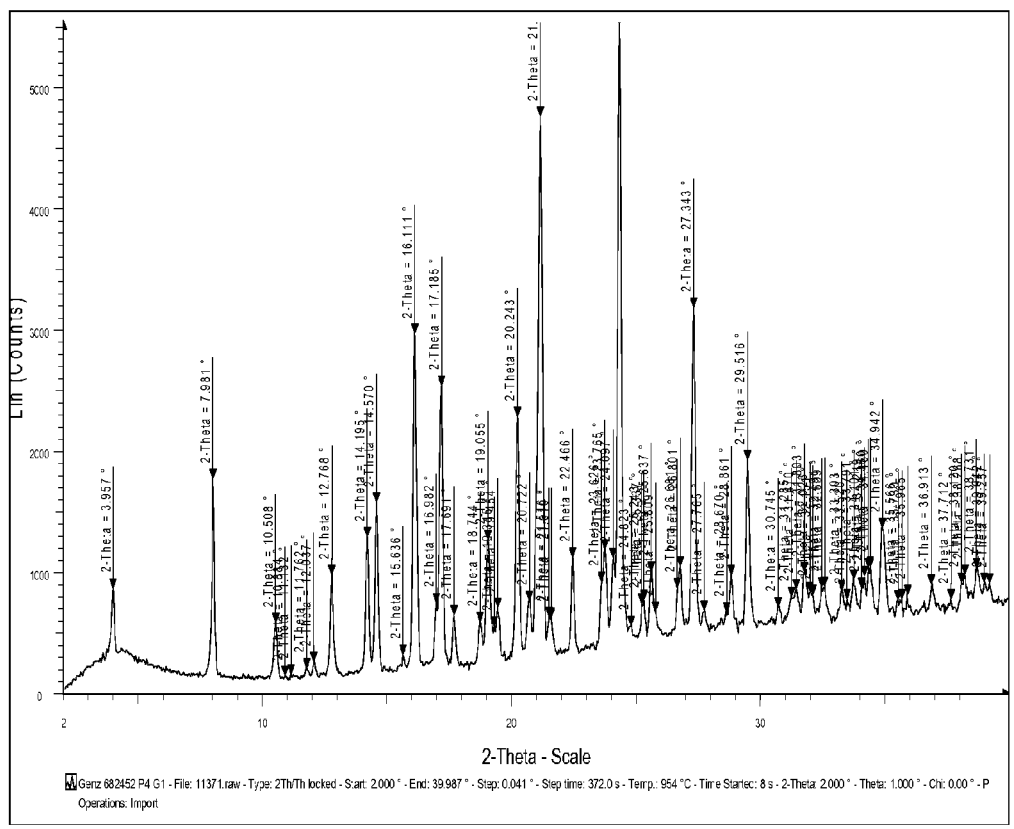
Figure 3:
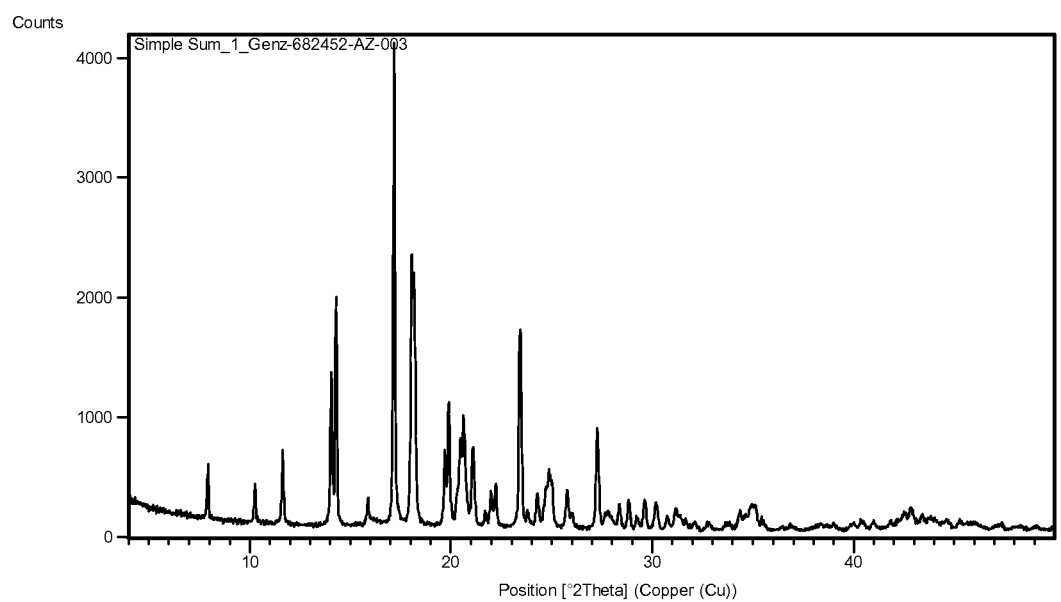
Figure 4:
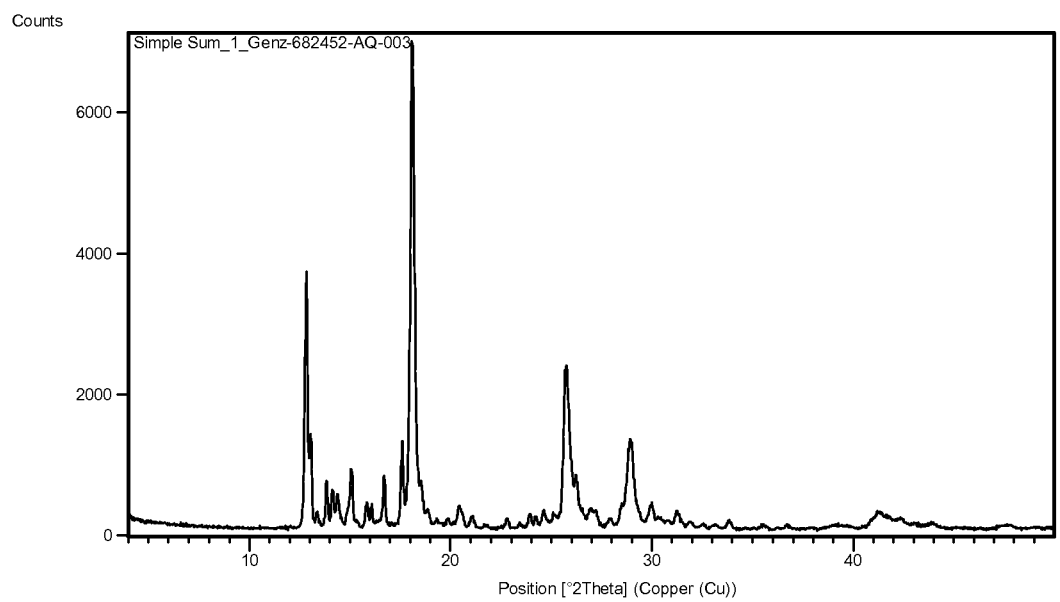

In certain embodiments of the invention, the small molecule therapy comprises administering to the subject an effective amount of (S)-Quinuclidin-3-yl (2-(2-(4-fluorophenyl)thiazol-4-yl)propan-2-yl)carbamate (see FIG. 2A). In other embodiments, the small molecule therapy comprises administering to the subject an effective amount of Quinuclidin-3-yl (2-(4'-fluoro-[1,1'-biphenyl]-3-yl)propan-2-yl)carbamate (see FIG. 2B). The small molecule therapy may include admininstering to a subject one or more compounds. In certain embodiments, at least one of the compounds is a compound of the present invention, such as those shown in FIGS. 2A and/or 2B.

Enzyme replacement therapy can provoke unwanted immune responses. Accordingly, immunosuppressant agents may be used together with an enzyme replacement therapy component of a combination therapy of the invention. Such agents may also be used with a small molecule therapy component, but the need for intervention here is generally less likely. Any immunosuppressant agent known to the skilled artisan may be employed together with a combination therapy of the invention. Such immunosuppressant agents include but are not limited to cyclosporine, FK506, rapamycin, CTLA4-Ig, and anti-TNF agents such as etanercept (see e.g. Moder, 2000, Ann. Allergy Asthma Immunol. 84, 280-284; Nevins, 2000, Curr. Opin. Pediatr. 12, 146-150; Kurlberg et al., 2000, Scand. J. Immunol. 51, 224-230; Ideguchi et al., 2000, Neuroscience 95, 217-226; Potter et al., 1999, Ann. N.Y. Acad. Sci. 875, 159-174; Slavik et al., 1999, Immunol. Res. 19, 1-24; Gaziev et al., 1999, Bone Marrow Transplant. 25, 689-696; Henry, 1999, Clin. Transplant. 13, 209-220; Gummert et al., 1999, J. Am. Soc. Nephrol. 10, 1366-1380; Qi et al., 2000, Transplantation 69, 1275-1283). The anti-IL2 receptor (.alpha.-subunit) antibody daclizumab (e.g. Zenapax™), which has been demonstrated effective in transplant patients, can also be used as an immunosuppressant agent (see e.g. Wiseman et al., 1999, Drugs 58, 1029-1042; Beniaminovitz et al., 2000, N. Engl J. Med. 342, 613-619; Ponticelli et al., 1999, Drugs R. D. 1, 55-60; Berard et al., 1999, Pharmacotherapy 19, 1127-1137; Eckhoff et al., 2000, Transplantation 69, 1867-1872; Ekberg et al., 2000, Transpl. Int. 13, 151-159). Additional immunosuppressant agents include but are not limited to anti-CD2 (Branco et al., 1999, Transplantation 68, 1588-1596; Przepiorka et al., 1998, Blood 92, 4066-4071), anti-CD4 (Marinova-Mutafchieva et al., 2000, Arthritis Rheum. 43, 638-644; Fishwild et al., 1999, Clin. Immunol. 92, 138-152), and anti-CD40 ligand (Hong et al., 2000, Semin. Nephrol. 20, 108-125; Chirmule et al., 2000, J. Virol. 74, 3345-3352; Ito et al., 2000, J. Immunol. 164, 1230-1235).

Any combination of immunosuppressant agents known to the skilled artisan can be used together with a combination therapy of the invention. One immunosuppressant agent combination of particular utility is tacrolimus (FK506) plus sirolimus (rapamycin) plus daclizumab (anti-IL2 receptor .alpha.-subunit antibody). This combination is proven effective as an alternative to steroids and cyclosporine, and when specifically targeting the liver. Moreover, this combination has recently been shown to permit successful pancreatic islet cell transplants. See Denise Grady, The New York Times, Saturday, May 27, 2000, pages A1 and A11. See also A. M. Shapiro et al., Jul. 27, 2000, "Islet Transplantation In Seven Patients With Type 1 Diabetes Mellitus Using A Glucocorticoid-Free Immunosuppressive Regimen", N. Engl. J. Med. 343, 230-238; Ryan et al., 2001, Diabetes 50, 710-719. Plasmaphoresis by any method known in the art may also be used to remove or deplete antibodies that may develop against various components of a combination therapy.

Immune status indicators of use with the invention include but are not limited to antibodies and any of the cytokines known to the skilled artisan, e.g., the interleukins, CSFs and interferons (see generally, Leonard et al., 2000, J. Allergy Clin. Immunol. 105, 877-888; Oberholzer et al., 2000, Crit. Care Med. 28 (4 Suppl.), N3-N12; Rubinstein et al., 1998, Cytokine Growth Factor Rev. 9, 175-181). For example, antibodies specifically immunoreactive with the replacement enzyme can be monitored to determine immune status of the subject. Among the two dozen or so interleukins known, particularly preferred immune status indicators are IL-1.alpha., IL-2, IL-4, IL-8 and IL-10. Among the colony stimulating factors (CSFs), particularly preferred immune status indicators are G-CSF, GM-CSF and M-CSF. Among the interferons, one or more alpha, beta or gamma interferons are preferred as immune status indicators.

In the sections which follow, various components that may be used for eight specific lysosomal storage diseases are provided (i.e., Gaucher (including types 1, 2 and 3), Fabry, Niemann-Pick B, Hunter, Morquio, Maroteaux-Lamy, Pompe, and Hurler-Scheie). In subsequent sections, further enabling disclosure for enzyme replacement therapy and small molecule therapy components of a combination therapy of the invention are provided.

Gaucher

As noted above, Gaucher's disease is caused by the deficiency of the enzyme glucocerebrosidase (beta-D-glucosyl-N-acylsphingosine glucohydrolase, EC 3.2.1.45) and accumulation of glucocerebroside (glucosylceramide). For an enzyme replacement therapy component of a combination therapy of the invention for the treatment of Gaucher's disease, a number of references are available which set forth satisfactory dosage regimens and other useful information relating to treatment (see Morales, 1996, Gaucher's Disease: A Review, The Annals of Pharmacotherapy 30, 381-388; Rosenthal et al., 1995, Enzyme Replacement Therapy for Gaucher Disease: Skeletal Responses to Macrophage-targeted Glucocerebrosidase, Pediatrics 96, 629-637; Barton et al., 1991, Replacement Therapy for Inherited Enzyme Deficiency—Macrophage-targeted Glucocerebrosidase for Gaucher's Disease, New England Journal of Medicine 324, 1464-1470; Grabowski et al., 1995, Enzyme Therapy in Type 1 Gaucher Disease: Comparative Efficacy of Mannose-terminated Glucocerebrosidase from Natural and Recombinant Sources, Annals of Internal Medicine 122, 33-39; Pastores et al., 1993, Enzyme Therapy in Gaucher Disease Type 1: Dosage Efficacy and Adverse Effects in 33 Patients treated for 6 to 24 Months, Blood 82, 408-416); and Weinreb et al., Am. J. Med.; 113(2):112-9 (2002).

In one embodiment, an ERT dosage regimen of from 2.5 units per kilogram (U/kg) three times a week to 60 U/kg once every two weeks is provided, where the enzyme is administered by intravenous infusion over 1-2 hours. A unit of glucocerebrosidase is defined as the amount of enzyme that catalyzes the hydrolysis of one micromole of the synthetic substrate para-nitrophenyl-p-D-glucopyranoside per minute at 37° C. In another embodiment, a dosage regimen of from 1 U/kg three times a week to 120 U/kg once every two weeks is provided. In yet another embodiment, a dosage regimen of from 0.25 U/kg daily or three times a week to 600 U/kg once every two to six weeks is provided.

Since 1991, alglucerase (Ceredase®) has been available from Genzyme Corporation. Alglucerase is a placentally-derived modified form of glucocerebrosidase. In 1994, imiglucerase (Cerezyme®) also became available from Genzyme Corporation. Imiglucerase is a modified form of glucocerebrosidase derived from expression of recombinant DNA in a mammalian cell culture system (Chinese hamster ovary cells). Imiglucerase is a monomeric glycoprotein of 497 amino acids containing four N-linked glycosylation sites. Imiglucerase has the advantages of a theoretically unlimited supply and a reduced chance of biological contaminants relative to placentally-derived aglucerase. These enzymes are modified at their glycosylation sites to expose mannose residues, a maneuver which improves lysosomal targeting via the mannose-6-phosphate receptor. Imiglucerase differs from placental glucocerebrosidase by one amino acid at position 495 where histidine is substituted for arginine. Several dosage regimens of these products are known to be effective (see Morales, 1996, Id.; Rosenthal et al., 1995, Id.; Barton et al., 1991, Id.; Grabowski et al., 1995, Id.; Pastores et al., 1993, Id.). For example, a dosage regimen of 60 U/kg once every two weeks is of clinical benefit in subjects with moderate to severe disease. The references cited above and the package inserts for these products should be consulted by the skilled practitioner for additional dosage regimen and administration information. See also U.S. Pat. Nos. 5,236,838 and 5,549,892 assigned to Genzyme Corporation.

As noted above, Gaucher Disease results from a deficiency of the lysosomal enzyme glucocerebrosidase (GC). In the most common phenotype of Gaucher disease (type 1), pathology is limited to the reticuloendothelial and skeletal systems and there are no neuropathic symptoms. See Barranger, Glucosylceramide lipidosis: Gaucher disease. In: Scriver C R B A, Sly W S, Valle D, editor. The Metabolic Basis of Inherited Disease. New York: McGraw-Hill. pp. 3635-3668 (2001). In neuropathic Gaucher disease (nGD), subdivided into type 2 and type 3 Gaucher disease, the deficiency of glucocerebrosidase (GC) causes glucosylceramide (GluCer; GL-1) and glucosylsphingosine (GluSph) to accumulate in the brain, leading to neurologic impairment. Type 2 Gaucher disease is characterized by early onset, rapid progression, extensive pathology in the viscera and central nervous system, and death usually by 2 years of age. Type 3 Gaucher disease, also known as subacute nGD, is an intermediate phenotype with varying age of onset and different degrees of severity and rates of progression. Goker-Alpan et al., The Journal of Pediatrics 143: 273-276 (2003). A recent development has produced the K14 lnl/lnl mouse model of type 2 Gaucher disease (hereinafter, the "K14 mouse"); this mouse model closely recapitulates the human disease showing ataxia, seizures, spasticity and a reduced median lifespan of only 14 days. Enquist et al., PNAS 104: 17483-17488 (2007).

As in patients with nGD, several mouse models of the disease have increased levels of GluCer and GluSph in the brain due to the deficiency in GC activity. Liu et al., PNAS 95: 2503-2508 (1998) and Nilsson, J. Neurochem 39: 709-718 (1982). The "K14" mice display a neuropathic phenotype that shares many pathologic features with type 2 Gaucher disease, such as neurodegeneration, astrogliosis, microglial proliferation, and increased levels of GluCer and GluSph in specific brain regions. Enquist et al. (2007).

Clinical management of patients affected by nGD poses a challenge for treating physicians both because of the severity of type 2 disease and the inability of the current therapies to cross the blood brain barrier (BBB). Current treatment of non-nGD relies on the intravenous delivery of recombinant human glucocerebrosidase (Imiglucerase; Cerezyme™) to replace the missing enzyme or the administration of glucosylceramide synthase inhibitors to attenuate substrate (GL-1) production. However, these drugs do not cross the blood brain barrier, and thus are not expected to provide therapeutic benefit for nGD patients. Current small molecule glucosylceramide synthase inhibitors in the clinic are not likely to address the neuropathic phenotypes of nGD. An evaluation of a compound of the present invention, Quinuclidin-3-yl (2-(4'-fluoro-[1,1'-biphenyl]-3-yl)propan-2-yl)carbamate (hereinafter, "Gz161"), in the K14 mouse model of type 2 Gaucher disease demonstrated that it could indeed reduce brain GluCer and GluSph (see Examples 122-125). It also reduced brain neuropathology and extended the lifespan of this model. Moreover, a combined approach using both enzyme replacement and small molecule substrate reduction may represent a superior therapy for type 2 Gaucher disease.

Fabry

As noted previously, Fabry's disease is caused by the deficiency of the lysosomal enzyme alpha-galactosidase A. The enzymatic defect leads to systemic deposition of glycosphingolipids having terminal alpha-galactosyl moieties, predominantly globotriaosylceramide (GL3 or Gb3) and, to a lesser extent, galabiosylceramide and blood group B glycosphingolipids.

Several assays are available to monitor disease progression and to determine when to switch from one treatment modality to another. In one embodiment, an assay to determine the specific activity of alpha-galactosidase A in a tissue sample may be used. In another embodiment, an assay to determine the accumulation of Gb3 may be used. In another embodiment, the practitioner may assay for deposition of glycosphingolipid substrates in body fluids and in lysosomes of vascular endothelial, perithelial and smooth muscle cells of blood vessels. Other clinical manifestations which may be useful indicators of disease management include proteinuria, or other signs of renal impairment such as red cells or lipid globules in the urine, and elevated erythrocyte sedimentation rate. One can also monitor anemia, decreased serum iron concentration, high concentration of beta-thromboglobulin, and elevated reticulocyte counts or platelet aggregation. Indeed, any approach for monitoring disease progression which is known to the skilled artisan may be used (See generally Desnick R J et al., 1995, .alpha.-Galactosidase A Deficiency: Fabry Disease, In: The Metabolic and Molecular Bases of Inherited Disease, Scriver et al., eds., McGraw-Hill, N.Y., 7.sup.th ed., pages 2741-2784). A preferred surrogate marker is pain for monitoring Fabry disease management. Other preferred methods include the measurement of total clearance of the enzyme and/or substrate from a bodily fluid or biopsy specimen. A preferred dosage regimen for enzyme replacement therapy in Fabry disease is 1-10 mg/kg i.v. every other day. A dosage regimen from 0.1 to 100 mg/kg i.v. at a frequency of from every other day to once weekly or every two weeks can be used.

Niemann-Pick B

As previously noted, Niemann-Pick B disease is caused by reduced activity of the lysosomal enzyme acid sphingomyelinase and accumulation of membrane lipid, primarily sphingomyelin. An effective dosage of replacement acid sphingomyelinase to be delivered may range from about 0.01 mg/kg to about 10 mg/kg body weight at a frequency of from every other day to weekly, once every two weeks, or once every two months. In other embodiments an effective dosage may range from about 0.03 mg/kg to about 1 mg/kg; from about 0.03 mg/kg to about 0.1 mg/kg; and/or from about 0.3 mg/kg to about 0.6 mg/kg. In a particular embodiment, a patient is administering acid sphingomyelinase in an escalating dose regimen at the following sequential doses: 0.1 mg/kg; 0.3 mg/kg; 0.6 mg/kg; and 1.0 mg/kg, wherein each dose of acid sphingomyelinase is administered at least twice, and each dose is administered at two week intervals, and wherein the patient is monitored for toxic side effects before elevating the dose to the next level (See U.S. Patent Application Publication No. 2011/0052559.

Hurler-Scheie (MPS I)

Hurler, Scheie, and Hurler-Scheie disease, also known as MPS I, are caused by inactivation of alpha-iduronidase and accumulation of dermatan sulfate and heparan sulfate. Several assays are available to monitor MPS I disease progression. For example, alpha-iduronidase enzyme activity can be monitored in tissue biopsy specimens or cultured cells obtained from peripheral blood. In addition, a convenient measure of disease progression in MPS I and other mucopolysaccharidoses is the urinary excretion of the glycosaminoglycans dermatan sulfate and heparan sulfate (see Neufeld et al., 1995, Id.). In a particular embodiment, alpha-iduronidase enzyme is administered once weekly as an intravenous infusion at a dosage of 0.58 mg/kg of body weight.

Hunter (MPS II)

Hunter's disease (a.k.a. MPS II) is caused by inactivation of iduronate sulfatase and accumulation of dermatan sulfate and heparan sulfate. Hunter's disease presents clinically in severe and mild forms. A dosage regimen of therapeutic enzyme from 1.5 mg/kg every two weeks to 50 mg/kg every week is preferred.

Morquio (MPS IV)

Morquio's syndrome (a.k.a. MPS IV) results from accumulation of keratan sulfate due to inactivation of either of two enzymes. In MPS IVA the inactivated enzyme is galactosamine-6-sulfatase and in MPS IVB the inactivated enzyme is beta-galactosidase. A dosage regimen of therapeutic enzyme from 1.5 mg/kg every two weeks to 50 mg/kg every week is preferred.

Maroteaux-Lamy (MPS VI)

Maroteaux-Lamy syndrome (a.k.a. MPS VI) is caused by inactivation of alactosamine-4-sulfatase (arylsulfatase B) and accumulation of dermatan sulfate. A dosage regimen of from 1.5 mg/kg every two weeks to 50 mg/kg every week is a preferred range of effective therapeutic enzyme provided by ERT. Optimally, the osage employed is less than or equal to 10 mg/kg per week. A preferred surrogate marker for MPS VI disease progression is roteoglycan levels.

Pompe

Pompe's disease is caused by inactivation of the acid alpha-glucosidase enzyme and accumulation of glycogen. The acid alpha-glucosidase gene resides on human chromosome 17 and is designated GAA. H. G. Hers first proposed the concept of inborn lysosomal disease based on his studies of this disease, which he referred to as type II glycogen storage disease (GSD II) and which is now also termed acid maltase deficiency (AMD) (see Hers, 1965, Gastroenterology 48, 625). In a particular embodiment, GAA is administered every 2 weeks as an intravenous infusion at a dosage of 20 mg/kg body weight.

Several assays are available to monitor Pompe disease progression. Any assay known to the skilled artisan may be used. For example, one can assay for intra-lysosomal accumulation of glycogen granules, particularly in myocardium, liver and skeletal muscle fibers obtained from biopsy. Alpha-glucosidase enzyme activity can also be monitored in biopsy specimens or cultured cells obtained from peripheral blood. Serum elevation of creatine kinase (CK) can be monitored as an indication of disease progression. Serum CK can be elevated up to ten-fold in infantile-onset patients and is usually elevated to a lesser degree in adult-onset patients. See Hirschhorn R, 1995, Glycogen Storage Disease Type II: Acid alpha-Glucosidase (Acid Maltase) Deficiency, In: The Metabolic and Molecular Bases of Inherited Disease, Scriver et al., eds., McGraw-Hill, N.Y., 7.sup.th ed., pages 2443-2464.

Enzyme Replacement Therapy

The following sections set forth specific disclosure and alternative embodiments available for the enzyme replacement therapy component of a combination therapy of the invention. Generally, dosage regimens for an enzyme replacement therapy component of a combination therapy of the invention are generally determined by the skilled clinician. Several examples of dosage regimens for the treatment of Gaucher's disease with glucocerebrosidase are provided above. The general principles for determining a dosage regimen for any given ERT component of a combination therapy of the invention for the treatment of any LSD will be apparent to the skilled artisan from publically available information, such as, for example, a review of the specific references cited in the sections for each specific LSD. An ERT may be administered to a patient by intravenous infusion. Intracerebroventricular and/or intrathecal infusion may be used (e.g., in addition to intravenous infusion) to administer ERT to a patient diagnosed with a lysosomal storage disease having CNS manifestations.

Any method known in the art may be used for the manufacture of the enzymes to be used in an enzyme replacement therapy component of a combination therapy of the invention. Many such methods are known and include but are not limited to the Gene Activation technology developed by Shire plc (see U.S. Pat. Nos. 5,968,502 and 5,272,071).

Small Molecule Therapy

The following section also sets forth specific disclosures and alternative embodiments available for the small molecule therapy component of a combination therapy of the invention. Dosage regimens for a small molecule therapy component of a combination therapy of the invention are generally determined by the skilled clinician and are expected to vary significantly depending on the particular storage disease being treated and the clinical status of the particular affected individual. The general principles for determining a dosage regimen for a given SMT component of any combination therapy of the invention for the treatment of any storage disease are well known to the skilled artisan. Guidance for dosage regimens can be obtained from any of the many well known references in the art on this topic. Further guidance is available, inter alia, from a review of the specific references cited herein.

Generally, compounds of the present invention, such as, for example, (S)-Quinuclidin-3-yl (2-(2-(4-fluorophenyl) thiazol-4-yl)propan-2-yl)carbamate and Quinuclidin-3-yl (2-(4'-fluoro-[1,1'-biphenyl]-3-yl)propan-2-yl)carbamate may be used in the combination therapies of the invention for treatment of virtually any storage disease resulting from a lesion in the glycosphingolipid pathway (e.g. Gaucher, Fabry, $G_{M1}$-gangliosidosis and $G_{M2}$-gangliosidoses (e.g., GM2 Activator Deficiency, Tay-Sachs and Sandhoff)). Likewise, aminoglycosides (e.g. gentamicin, G418) may be used in the combination therapies of the invention for any storage disease individual having a premature stop-codon mutation (i.e., nonsense mutation). Such mutations are particularly prevalent in Hurler syndrome. A small molecule therapy component of a combination therapy of the invention is particularly preferred where there is a central nervous system manifestation to the storage disease being treated (e.g., Sandhoff, Tay-Sachs, Niemann-Pick Type A, and Gaucher types 2 and 3), since small molecules can generally cross the blood-brain barrier with ease when compared to other therapies.

Preferred dosages of substrate inhibitors used in a combination therapy of the invention are easily determined by the skilled artisan. In certain embodiments, such dosages may range from about 0.5 mg/kg to about 300 mg/kg, preferably from about 5 mg/kg to about 60 mg/kg (e.g., 5 mg/kg, 10 mg/kg, 15, mg/kg, 20 mg/kg, 25 mg/kg, 30 mg/kg, 35 mg/kg, 40 mg/kg, 45 mg/kg, 50 mg/kg, 55 mg/kg and 60 mg/kg) by intraperitoneal, oral or equivalent administration from one to five times daily. Such dosages may range from about 5 mg/kg to about 5 g/kg, preferably from about 10 mg/kg to about 1 g/kg by oral, intraperitoneal or equivalent administration from one to five times daily. In one embodiment, doses range from about about 10 mg/day to about 500 mg/day (e.g., 10 mg/day, 20 mg/day, 30 mg/day, 40 mg/day, 50 mg/day, 60 mg/day, 70 mg/day, 80 mg/day, 90 mg/day, 100 mg/day, 110 mg/day, 120 mg/day, 130 mg/day, 140 mg/day, 150 mg/day, 160 mg/day, 170 mg/day, 180 mg/day, 190 mg/day, 200 mg/day, 210 mg/day, 220 mg/day, 230 mg/day, 240 mg/day, 250 mg/day, 260 mg/day, 270 mg/day, 280 mg/day, 290 mg/day, 300 mg/day). A particularly preferred oral dose range is from about 50 mg to about 100 mg, wherein the dose is administered twice daily. A particular oral dose range for a compound of the present invention is from about 5 mg/kg/day to about 600 mg/kg/day. In a particular oral dose range for a compound of the present invention is from about 1 mg/kg/day to about 100 mg/kg/day, e.g., 1 mg/kg/day, 5 mg/kg/day, 10 mg/kg/day, 15 mg/kg/day, 20 mg/kg/day, 25 mg/kg/day, 30 mg/kg/day, 35 mg/kg/day, 40 mg/kg/day, 45 mg/kg/day, 50 mg/kg/day, 55 mg/kg/day or 60 mg/kg/day, 65 mg/kg/day, 70 mg/kg/day, 75 mg/kg/day, 80 mg/kg/day, 85 mg/kg/day, 90 mg/kg/day, 95 mg/kg/day or 100 mg/kg/day.

A rotating combination of therapeutic platforms (i.e., enzyme replacement and small molecule therapy) is preferred. However, subjects may also be treated by overlapping both approaches as needed, as determined by the skilled clinician. Examples of treatment schedules may include but are not limited to: (1) SMT followed by ERT; (2) ERT followed by SMT; and (3) ERT and SMT provided at about the same time. As noted previously, temporal overlap of therapeutic platforms may also be performed, as needed, depending on the clinical course of a given storage disease in a given subject.

Treatment intervals for various combination therapies can vary widely and may generally be different among different storage diseases and different individuals depending on how aggressively storage products are accumulated. For example, Fabry storage product accumulation may be slow compared to rapid storage product accumulation in Pompe. Titration of a particular storage disease in a particular individual is carried out by the skilled artisan by monitoring the clinical signs of disease progression and treatment success.

The various macromolecules that accumulate in lysosomal storage diseases are not uniformly distributed, but instead are deposited in certain preferred anatomic sites for each disease. However, an exogenously supplied enzyme is generally taken up by cells of the reticuloendothelial system and sorted to the lysosomal compartment where it acts to hydrolyze the accumulated substrate. Moreover, cellular uptake of therapeutic enzyme can be augmented by certain maneuvers to increase lysosomal targeting (see e.g. U.S. Pat. No. 5,549,892 by Friedman et al., assigned to Genzyme Corporation, which describes recombinant glucocerebrosidase having improved pharmacokinetics by virtue of remodeled oligosaccharide side chains recognized by cell surface mannose receptors which are endocytosed and transported to lysosomes).

Some treatment modalities target some affected organs better than others. In Fabry, for example, if ERT does not reach the kidney well enough for a satisfactory clinical outcome, SMT can be used to reduce the substrate levels in the kidney. As demonstrated in Example 112 and FIG. 6B, SMT effectively reduced Gb3 levels (i.e., the substrate accumulated in Fabry patients) in the urine of a Fabry mouse model to a greater extent than ERT. The kidneys are believed to be the major source of urine Gb3. In contrast, FIG. 6B shows ERT effectively reduced the Gb3 levels in the plasma to a greater extent than SMT. These results demonstrate that a combination therapy of ERT and SMT provides a complementary therapeutic strategy that takes advantage of the strengths and addresses the weaknesses associated with each therapy employed alone. SMT is able to cross the BBB, providing a powerful approach, when combined with ERT, for treating LSDs having CNS manifestations, such as Niemann Pick Type A and Neuropathic Gaucher disease (nGD). Moreover, substrate reduction by SMT combined with enzyme replacement address the storage problem at separate and distinct intervention points which may enhance clinical outcome.

It will be understood that reference to simultaneous or concurrent administration of two or more therapies does not require that they be administered at the same time, just that they be acting in the subject at the same time.

Example 1

(S)-Quinuclidin-3-yl (2-(2-(4-fluorophenyl)thiazol-4-yl)propan-2-yl)carbamate

Step 1: Dimethylation with Methyl Iodide

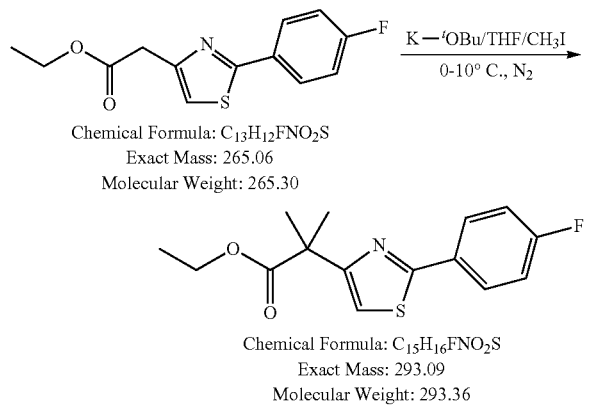

Procedure:

A 3N RB flask was equipped with a thermometer, an addition funnel and a nitrogen inlet. The flask was flushed with nitrogen and potassium tert-butoxide (MW 112.21, 75.4 mmol, 8.46 g, 4.0 equiv., white powder) was weighed out and added to the flask via a powder funnel followed by the addition of THF (60 mL). Most of the potassium tert-butoxide dissolves to give a cloudy solution. This mixture was cooled in an ice-water bath to 0-2° C. (internal temperature). In a separate flask, the starting ester (MW 265.3, 18.85 mmol, 5.0 g, 1.0 equiv.) was dissolved in THF (18 mL+2 mL as rinse) and transferred to the addition funnel. This solution was added drop wise to the cooled mixture over a period of 25-30 min, keeping the internal temperature below 5° C. during the addition. The reaction mixture was cooled back to 0-2° C. In a separate flask, a solution of methyl iodide (MW 141.94, 47.13 mmol, 6.7 g, 2.5 equiv.) in THF (6 mL) was prepared and transferred to the addition funnel. The flask containing the methyl iodide solution was then rinsed with THF (1.5 mL) which was then transferred to the addition funnel already containing the clear colorless solution of methyl iodide in THF. This solution was added carefully drop wise to the dark brown reaction mixture over a period of 30-40 min, keeping the internal temperature below 10° C. at all times during the addition. After the addition was complete, the slightly turbid mixture was stirred for an additional 1 h during which time the internal temperature drops to 0-5° C. After stirring for an hour at 0-5° C., the reaction mixture was quenched with the slow drop wise addition of 5.0M aqueous HCl (8 mL) over a period of 5-7 min. The internal temperature should be maintained below 20° C. during this addition. After the addition, water (14 mL) was added and the mixture was stirred for 2-3 min. The stirring was stopped and the 2 layers are allowed to separate. The 2 layers are then transferred to a 250 mL 1N RB flask and the THF was evaporated in vacuo as much as possible to obtain a biphasic layer of THF/product and water. The 2 layers are allowed to separate. A THF solution of the Step 1 product was used in the next reaction.

Step 2: Hydrolysis of the Ethyl Ester with LiOH Monohydrate

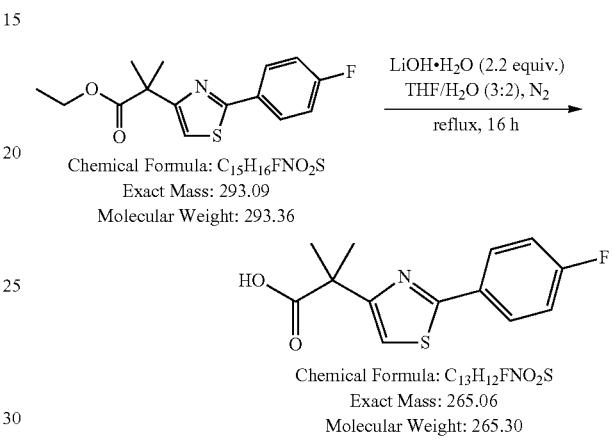

Procedure: The crude ester in THF was added to the reaction flask. Separately, LiOH.H2O (MW 41.96, 75.0 mmol, 3.15 grams, 2.2 equiv.) was weighed out in a 100 mL beaker to which a stir bar was added. Water (40 mL) was added and the mixture was stirred till all the solid dissolves to give a clear colorless solution. This aqueous solution was then added to the 250 mL RB flask containing the solution of the ester in tetrahydrofuran (THF). A condenser was attached to the neck of the flask and a nitrogen inlet was attached at the top of the condenser. The mixture was heated at reflux for 16 hours. After 16 hours, the heating was stopped and the mixture was cooled to room temperature. The THF was evaporated in vacuo to obtain a brown solution. An aliquot of the brown aqueous solution was analyzed by HPLC and LC/MS for complete hydrolysis of the ethyl ester. Water (15 mL) was added and this aqueous basic solution was extracted with TBME (2×40 mL) to remove the t-butyl ester. The aqueous basic layer was cooled in an ice-water bath to 0-10° C. and acidified with dropwise addition of concentrated HCl to pH~1 with stirring. To this gummy solid in the aqueous acidic solution was added TBME (60 mL) and the mixture was shaken and then stirred vigorously to dissolve all the acid into the TBME layer. The 2 layers are transferred to a separatory funnel and the TBME layer was separated out. The pale yellow aqueous acidic solution was re-extracted with TBME (40 mL) and the TBME layer was separated and combined with the previous TBME layer. The aqueous acidic layer was discarded. The combined TBME layers are dried over anhydrous $Na_2SO_4$, filtered and evaporated in vacuo to remove TBME and obtain the crude acid as orange/dark yellow oil that solidifies under high vacuum to a dirty yellow colored solid. The crude acid was weighed out and crystallized by heating it in heptane/TBME (3:1, 5 mL/g of crude) to give the acid as a yellow solid.

Step 3: Formation of Hydroxamic Acid with NH₂OH.HCl

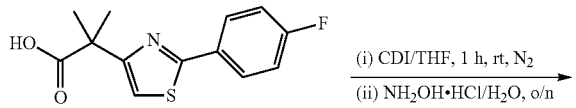

Chemical Formula: C₁₃H₁₂FNO₂S
Exact Mass: 265.06
Molecular Weight: 265.30

(i) CDI/THF, 1 h, rt, N₂
(ii) NH₂OH·HCl/H₂O, o/n

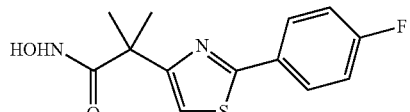

Chemical Formula: C₁₃H₁₃FN₂O₂S
Exact Mass: 280.07
Molecular Weight: 280.32

Procedure:

The carboxylic acid (MW 265.3, 18.85 mmol, 5.0 g, 1.0 equiv.) was weighed and transferred to a 25 mL 1N RB flask under nitrogen. THF (5.0 mL) was added and the acid readily dissolves to give a clear dark yellow to brown solution. The solution was cooled to 0-2° C. (bath temperature) in an ice-bath and N,N'-carbonyldiimidazole (CDI; MW 162.15, 20.74 mmol, 3.36 g, 1.1 equiv.) was added slowly in small portions over a period of 10-15 min. The ice-bath was removed and the solution was stirred at room temperature for 1 h. After 1 h of stirring, the solution was again cooled in an ice-water bath to 0-2° C. (bath temperature). Hydroxylamine hydrochloride (NH₂OH.HCl; MW 69.49, 37.7 mmol, 2.62 g, 2.0 equiv.) was added slowly in small portions as a solid over a period of 3-5 min as this addition was exothermic. After the addition was complete, water (1.0 mL) was added to the heterogeneous mixture dropwise over a period of 2 min and the reaction mixture was stirred at 0-10° C. in the ice-water bath for 5 min. The cooling bath was removed and the reaction mixture was stirred under nitrogen at room temperature overnight for 20-22 h. The solution becomes clear as all the NH₂OH.HCl dissolves. After 20-22 h, an aliquot of the reaction mixture was analyzed by High Pressure Liquid Chromatography (HPLC). The THF was then evaporated in vacuo and the residue was taken up in dichloromethane (120 mL) and water (60 mL). The mixture was transferred to a separatory funnel where it was shaken and the 2 layers are allowed to separate. The water layer was discarded and the dichloromethane layer was washed with 1N hydrochloride (HCl; 60 mL). The acid layer was discarded. The dichloromethane layer was dried over anhydrous Na₂SO₄, filtered and the solvent evaporated in vacuo to obtain the crude hydroxamic acid as a pale yellow solid that was dried under high vacuum overnight.

Step 3 Continued: Conversion of Hydroxamic Acid to Cyclic Intermediate (not Isolated)

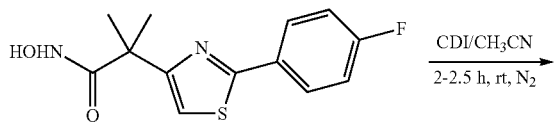

Chemical Formula: C₁₃H₁₃FN₂O₂S
Exact Mass: 280.07
Molecular Weight: 280.32

CDI/CH₃CN
2-2.5 h, rt, N₂

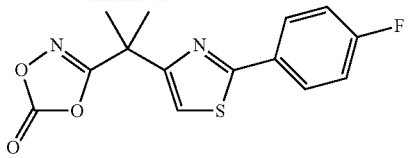

Chemical Formula: C₁₄H₁₁FN₂O₃S
Exact Mass: 306.05
Molecular Weight: 306.31

Procedure:

The crude hydroxamic acid (MW 280.32, 5.1 g) was transferred to a 250 mL 1N RB flask with a nitrogen inlet. A stir bar was added followed by the addition of acetonitrile (50 mL). The solid was insoluble in acetonitrile. The yellow heterogeneous mixture was stirred for 2-3 min under nitrogen and CDI (MW 162.15, 20.74 mmol, 3.36 g, 1.1 equiv.) was added in a single portion at room temperature. No exotherm was observed. The solid immediately dissolves and the clear yellow solution was stirred at room temperature for 2-2.5 h. After 2-2.5 h, an aliquot was analyzed by HPLC and LC/MS which shows conversion of the hydroxamic acid to the desired cyclic intermediate.

The acetonitrile was then evaporated in vacuo to give the crude cyclic intermediate as reddish thick oil. The oil was taken up in toluene (60 mL) and the reddish mixture was heated to reflux for 2 hours during which time, the cyclic intermediate releases CO₂ and rearranges to the isocyanate (see below).

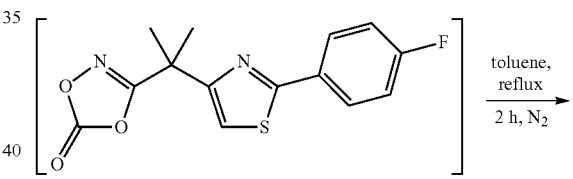

Chemical Formula: C₁₄H₁₁FN₂O₃S
Exact Mass: 306.05
Molecular Weight: 306.31 toluene, reflux
2 h, N₂

Chemical Formula: C₁₃H₁₁FN₂OS
Exact Mass: 262.06
Molecular Weight: 262.30

Step 3 Continued: Conversion of the Isocyanate to the Free Base

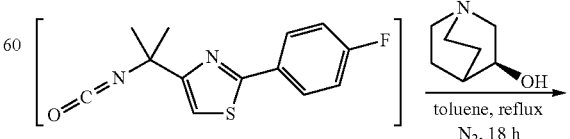

Chemical Formula: C₁₃H₁₁FN₂OS
Exact Mass: 262.06
Molecular Weight: 262.30 toluene, reflux
N₂, 18 h

-continued

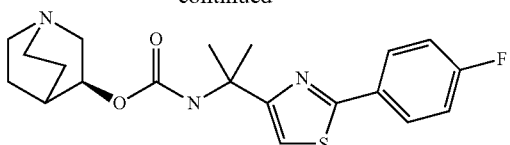

Chemical Formula: C₂₀H₂₄FN₃O₂S
Exact Mass: 389.16
Molecular Weight: 389.49

The reaction mixture was cooled to 50-60° C. and (S)-(+)-quinuclidinol (MW 127.18, 28.28 mmol, 3.6 g, 1.5 equiv.) was added to the mixture as a solid in a single portion. The mixture was re-heated to reflux for 18 h. After 18 h, an aliquot was analyzed by HPLC and LC/MS which shows complete conversion of the isocyanate to the desired product. The reaction mixture was transferred to a separatory funnel and toluene (25 mL) was added. The mixture was washed with water (2×40 mL) and the water layers are separated. The combined water layers are re-extracted with toluene (30 mL) and the water layer was discarded. The combined toluene layers are extracted with 1N HCl (2×60 mL) and the toluene layer (containing the O-acyl impurity) was discarded. The combined HCl layers are transferred to a 500 mL Erlenmeyer flask equipped with a stir bar. This stirring clear yellow/reddish orange solution was basified to pH 10-12 by the dropwise addition of 50% w/w aqueous NaOH. The desired free base precipitates out of solution as a dirty yellow gummy solid which could trap the stir bar. To this mixture was added isopropyl acetate (100 mL) and the mixture was stirred vigorously for 5 min when the gummy solid goes into isopropyl acetate. The stirring was stopped and the 2 layers are allowed to separate. The yellow isopropyl acetate layer was separated and the basic aqueous layer was re-extracted with isopropyl acetate (30 mL). The basic aqueous layer was discarded and the combined isopropyl acetate layers are dried over anhydrous Na₂SO₄, filtered into a pre-weighed RB flask and the solvent evaporated in vacuo to obtain the crude free base as beige to tan solid that was dried under high vacuum overnight.

Step 3 Continued: Recrystallization of the Crude Free Base

The beige to tan colored crude free base was weighed and re-crystallized from heptane/isopropyl acetate (3:1, 9.0 mL of solvent/g of crude free base). The appropriate amount of heptane/isopropyl acetate was added to the crude free base along with a stir bar and the mixture (free base was initially partially soluble but dissolves to give a clear reddish orange solution when heated to reflux) was heated to reflux for 10 min. The heat source was removed and the mixture was allowed to cool to room temperature with stirring when a white precipitate forms. After stirring at room temperature for 3-4 h, the precipitate was filtered off under hose vacuum using a Buchner funnel, washed with heptane (20 mL) and dried under hose vacuum on the Buchner funnel overnight. The precipitate was the transferred to a crystallizing dish and dried at 55° C. overnight in a vacuum oven. $^1$H NMR (400 MHz, CDCl₃) δ 8.04-7.83 (m, 2H), 7.20-6.99 (m, 3H), 5.53 (s, 1H), 4.73-4.55 (m, 1H), 3.18 (dd, J=14.5, 8.4 Hz, 1H), 3.05-2.19 (m, 5H), 2.0-1.76 (m, 11H). $^{13}$C NMR (100 MHz, CDCl₃) δ 166.38, 165.02, 162.54, 162.8-155.0 (d, C—F), 130.06, 128.43, 128.34, 116.01, 115.79, 112.46, 71.18, 55.70, 54.13, 47.42, 46.52, 27.94, 25.41, 24.67, 19.58.

Example 2

Crystalline Form A of (S)-Quinuclidin-3-yl (2-(2-(4-fluorophenyl)thiazol-4-yl)propan-2-yl)carbamate malate The free base of (S)-Quinuclidin-3-yl (2-(2-(4-fluorophenyl)thiazol-4-yl)propan-2-yl)carbamate (20 g) was dissolved IPA (140 ml) at room temperature and filtered. The filtrate was added into a 1 L r.b. flask which was equipped with an overhead stirrer and nitrogen in/outlet. L-malic acid (6.89 g) was dissolved in IPA (100+30 ml) at room temperature and filtered. The filtrate was added into the above 1 Liter flask. The result solution was stirred at room temperature (with or without seeding) under nitrogen for 4-24 hours. During this period of time crystal came. The product was collected by filtration and washed with a small amount of IPA (30 ml). The solid was dried in a vacuum oven at 55° C. for 72 hours (23 g, yield).

H$^1$ NMR CDCl3

| δ (ppm) | splitting | Integral | assignment |
|---------|-----------|----------|------------|
| 7.9 | m | 2 | Ha |
| 7.1 | m | 3 | Hb, Hc |
| 5.9 | br s | 1 | NH |
| 4.9 | m | 1 | Hd |
| 4.2 | m | 1 | Ha' |
| 3.1-3.6 | m | 6 | He |
| 2.7 | m | 2 | Hb' |
| 1.6-2.4 | m | 11 | Hf, (CH₃)₂ |

Example 3

(S)-Quinuclidin-3-yl (2-(2-(4-fluorophenyl)thiazol-4-yl)propan-2-yl)carbamate HCl salt (S)-Quinuclidin-3-yl (2-(2-(4-fluorophenyl)thiazol-4-yl)propan-2-yl)carbamate (0.78 g, 2 mmole) in IPA (8 ml) was stirred at room temperature HCl (2 M in IPA, 1 ml) was added. The solution was seeded and stirred at room temperature for 18 h. The product was collected by filtration and dried under vacuum to product (0.7 g). $^1$H NMR (400 MHz, CDCl3) δ 12. (br, s, 1H), 7.9-8.0 (m, 2H), 7.1-7.2 (m, 3H), 5.9 (br, s, 1H), 4.9-5.0 (m, 1H), 3.2-3.6 (m, 6H), 1.7-2.4 (m, 11H).

Example 3

(S)-Quinuclidin-3-yl (2-(2-(4-fluorophenyl)thiazol-4-yl)propan-2-yl)carbamate (S)-2-hydroxysuccinate salt Succinic acid (0.15 g) was dissolved in IPA (5 ml) and stirred at 50° C. (S)-Quinuclidin-3-yl (2-(2-(4-fluorophenyl)thiazol-4-yl)propan-2-yl)carbamate (0.5 g) in IPA (8 ml) was added. The solution was seeded and stirred at room temperature for 20 h. The product was collected by filtration and dried under vacuum to product (0.4 g). $^1$H NMR (400 MHz, CDCl3) δ 7.9 (m, 2H), 7.1-7.2 (m, 3H), 5.8 (br, s, 1H), 4.9 (m, 1H), 3.1-3.5 (m, 6H), 2.6 (s, 4H), 1.7-2.4 (m, 11H).

The invention claimed is:
1. A crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peak measured using CuK$_\alpha$ radiation: 18.095.

2. A crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095 and 17.493.

3. A crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095 and 19.516.

4. A crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095, 17.493, and 19.516.

5. A crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095, 17.493, 19.516 and 20.088.

6. A crystalline Form A of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 18.095, 17.493, 19.516 and 20.088 and 17.125.

7. A crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peak measured using CuK$_\alpha$ radiation: 24.355.

8. A crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355 and 21.167.

9. A crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355, 21.167 and 27.343.

10. A crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355, 21.167, 27.343 and 16.111.

11. A crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355, 21.167, 27.343, 16.111 and 17.185.

12. A crystalline Form B of (S)-Quinuclidin-3-yl (2-(2-(4-fluorophenyl)thiazol-4-yl)propan-2-yl)carbamate malate, wherein said x-ray powder diffraction contains the following 2-theta peaks measured using CuK$_\alpha$ radiation: 24.355, 21.167, 27.343, 16.111, 17.185 and 20.243.

13. A crystalline form of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peak measured using CuK$_\alpha$ radiation: 17.162.

14. A crystalline Form A of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162 and 18.028.

15. A crystalline form of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162 and 14.280.

16. A crystalline form of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162, 18.028 and 14.280.

17. A crystalline form of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162, 18.028, 14.280 and 18.153.

18. A crystalline form of (S)-Quinuclidin-3-yl (2-(2-(4-fluorophenyl)thiazol-4-yl)propan-2-yl)carbamate (S)-2-hydroxysuccinate salt, wherein said x-ray powder diffraction contains the following 2-theta peaks measured using CuK$_\alpha$ radiation: 17.162, 18.028, 14.280, 18.153 and 23.422.

19. A crystalline form of (S)-Quinuclidin-3-yl (2-(2-(4-fluorophenyl)thiazol-4-yl)propan-2-yl)carbamate HCl salt, wherein said x-ray powder diffraction contains the following 2-theta peak measured using CuK$_\alpha$ radiation: 18.087.

20. A crystalline form of (S)-Quinuclidin-3-yl (2-(2-(4-fluorophenyl)thiazol-4-yl)propan-2-yl)carbamate HCl salt, wherein said x-ray powder diffraction contains the following 2-theta peak measured using CuK$_\alpha$ radiation: 12.818.

21. A crystalline form of (S)-Quinuclidin-3-yl (2-(2-(4-fluorophenyl)thiazol-4-yl)propan-2-yl)carbamate HCl salt, wherein said x-ray powder diffraction contains the following 2-theta peak measured using CuK$_\alpha$ radiation: 25.722.

22. A crystalline form of (S)-Quinuclidin-3-yl (2-(2-(4-fluorophenyl)thiazol-4-yl)propan-2-yl)carbamate HCl salt, wherein said x-ray powder diffraction contains the following 2-theta peaks measured using CuK$_\alpha$ radiation: 12.818 and 25.722.

23. A crystalline form of (S)-Quinuclidin-3-yl (2-(2-(4-fluorophenyl)thiazol-4-yl)propan-2-yl)carbamate HCl salt, wherein said x-ray powder diffraction contains the following 2-theta peaks measured using CuK$_\alpha$ radiation: 12.818, 25.722 and 13.040.

24. A crystalline form of (S)-Quinuclidin-3-yl (2-(2-(4-fluorophenyl)thiazol-4-yl)propan-2-yl)carbamate HCl salt, wherein said x-ray powder diffraction contains the following 2-theta peaks measured using CuK$_\alpha$ radiation: 12.818, 25.722, 13.040 and 28.910.

* * * * *